(12) United States Patent
Hanson et al.

(10) Patent No.: US 9,351,746 B2
(45) Date of Patent: May 31, 2016

(54) COORDINATE MAPPING SYSTEM FOR JOINT TREATMENT

(71) Applicant: ZIMMER KNEE CREATIONS, INC., Exton, PA (US)

(72) Inventors: Shaun B. Hanson, West Chester, PA (US); Christopher D. Mandeen, West Chester, PA (US); Thomas A. Russell, Eads, TN (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 0 days.

(21) Appl. No.: 14/508,436

(22) Filed: Oct. 7, 2014

(65) Prior Publication Data

US 2015/0025589 A1 Jan. 22, 2015

Related U.S. Application Data

(63) Continuation of application No. 12/950,114, filed on Nov. 19, 2010, now Pat. No. 8,864,768.

(60) Provisional application No. 61/311,632, filed on Mar. 8, 2010, provisional application No. 61/263,170, filed on Nov. 20, 2009.

(51) Int. Cl.
*A61B 17/17* (2006.01)
*A61B 19/00* (2006.01)
*A61B 17/34* (2006.01)

(52) U.S. Cl.
CPC .......... *A61B 17/1764* (2013.01); *A61B 19/201* (2013.01); *A61B 2017/3411* (2013.01); *A61B 2019/5437* (2013.01); *A61B 2019/5466* (2013.01)

(58) Field of Classification Search
CPC .......................... A61B 17/1764; A61B 19/201
See application file for complete search history.

(56) References Cited

U.S. PATENT DOCUMENTS 2,697,433 A 12/1954 Zehnder
3,913,187 A 10/1975 Okuida
(Continued)

FOREIGN PATENT DOCUMENTS

CN 101048111 A 10/2007
CN 101102724 A 1/2008
(Continued)

OTHER PUBLICATIONS

"U.S. Appl. No. 12/950,154, Notice of Allowance mailed Oct. 10, 2014", 6 pgs.
(Continued)

*Primary Examiner* — Andrew Yang
(74) *Attorney, Agent, or Firm* — Schwegman Lundberg & Woessner, P.A.

(57) ABSTRACT

A coordinate mapping system is provided for locating a defect in a bone. The system comprises a positioning instrument for controlled delivery of a device to a target site, the instrument comprising a main body and a rail extending from the main body, the rail including a series of indicia corresponding to predefined grid lines, and a template configured to overlay an image of a bone having a defect at the target site, the template including a predefined grid for determining a set of coordinates to locate the target site using the positioning instrument. A method of accessing a target site near a defect in a bone using the radial coordinate mapping system is also provided.

18 Claims, 16 Drawing Sheets

(56) References Cited

U.S. PATENT DOCUMENTS

| | | | |
|---|---|---|---|
| 3,988,783 A | 11/1976 | Treace | |
| 4,037,592 A | 7/1977 | Kronner | |
| 4,108,165 A | 8/1978 | Kopp et al. | |
| 4,360,012 A | 11/1982 | Mcharrie et al. | |
| 4,653,487 A | 3/1987 | Maale | |
| 4,781,182 A | 11/1988 | Purnell et al. | |
| 4,815,454 A | 3/1989 | Dozier, Jr. | |
| 4,883,048 A | 11/1989 | Purnell et al. | |
| 4,911,153 A | 3/1990 | Border | |
| 4,920,958 A | 5/1990 | Walt et al. | |
| 4,964,861 A | 10/1990 | Agee et al. | |
| 5,098,383 A | 3/1992 | Hemmy et al. | |
| 5,163,940 A | 11/1992 | Bourque | |
| 5,178,164 A | 1/1993 | Allen | |
| 5,247,934 A | 9/1993 | Wehrli et al. | |
| 5,298,254 A | 3/1994 | Prewett et al. | |
| 5,324,295 A | 6/1994 | Shapiro | |
| 5,342,363 A | 8/1994 | Richelsoph | |
| 5,370,646 A | 12/1994 | Reese et al. | |
| 5,439,684 A | 8/1995 | Prewett et al. | |
| 5,458,602 A | 10/1995 | Goble et al. | |
| 5,514,137 A | 5/1996 | Coutts | |
| 5,556,429 A | 9/1996 | Felt | |
| 5,595,193 A | 1/1997 | Walus et al. | |
| 5,609,636 A | 3/1997 | Kohrs et al. | |
| 5,618,549 A | 4/1997 | Patat et al. | |
| 5,681,320 A | 10/1997 | McGuire | |
| 5,741,266 A | 4/1998 | Moran et al. | |
| 5,743,916 A | 4/1998 | Greenberg et al. | |
| 5,755,809 A | 5/1998 | Cohen et al. | |
| 5,766,221 A | 6/1998 | Benderev et al. | |
| 5,827,289 A | 10/1998 | Reiley et al. | |
| 5,868,749 A | 2/1999 | Reed | |
| 5,888,220 A | 3/1999 | Felt et al. | |
| 5,891,150 A | 4/1999 | Chan | |
| 5,928,239 A | 7/1999 | Mirza | |
| 5,968,047 A | 10/1999 | Reed | |
| 5,968,050 A | 10/1999 | Torrie | |
| 5,972,015 A | 10/1999 | Scribner et al. | |
| 6,010,502 A | 1/2000 | Bagby | |
| 6,036,696 A | 3/2000 | Lambrecht et al. | |
| 6,039,742 A | 3/2000 | Krettek et al. | |
| 6,048,346 A | 4/2000 | Reiley et al. | |
| 6,066,154 A | 5/2000 | Reiley et al. | |
| 6,110,211 A | 8/2000 | Weiss | |
| 6,111,164 A | 8/2000 | Rainey et al. | |
| 6,120,511 A | 9/2000 | Chan | |
| 6,140,452 A | 10/2000 | Felt et al. | |
| 6,143,030 A | 11/2000 | Schroder | |
| 6,162,225 A | 12/2000 | Gertzman et al. | |
| 6,214,013 B1 | 4/2001 | Lambrecht et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,248,131 B1 | 6/2001 | Felt et al. | |
| 6,254,605 B1 | 7/2001 | Howell | |
| 6,267,770 B1 | 7/2001 | Truwit | |
| 6,270,528 B1 | 8/2001 | Mckay | |
| 6,283,942 B1 | 9/2001 | Staehlin et al. | |
| 6,285,901 B1 | 9/2001 | Taicher et al. | |
| 6,287,313 B1 | 9/2001 | Sasso | |
| 6,294,187 B1 | 9/2001 | Boyce et al. | |
| 6,306,177 B1 | 10/2001 | Felt et al. | |
| 6,342,056 B1 | 1/2002 | Mac-Thiong et al. | |
| 6,358,251 B1 | 3/2002 | Mirza | |
| 6,368,322 B1 | 4/2002 | Luks et al. | |
| 6,395,007 B1 | 5/2002 | Bhatnagar et al. | |
| 6,398,811 B1 | 6/2002 | Mckay | |
| 6,423,083 B2 | 7/2002 | Reiley et al. | |
| 6,486,232 B1 | 11/2002 | Wise et al. | |
| 6,506,192 B1 | 1/2003 | Gertzman et al. | |
| 6,506,785 B2 | 1/2003 | Evans et al. | |
| 6,520,969 B2 | 2/2003 | Lambrecht et al. | |
| 6,527,773 B1 | 3/2003 | Lin et al. | |
| 6,533,794 B2 | 3/2003 | Chakeres | |
| 6,564,083 B2 | 5/2003 | Stevens | |
| 6,607,561 B2 | 8/2003 | Brannon | |
| 6,613,054 B2 | 9/2003 | Scribner et al. | |
| 6,645,213 B2 | 11/2003 | Sand et al. | |
| 6,663,647 B2 | 12/2003 | Reiley et al. | |
| 6,719,761 B1 | 4/2004 | Reiley et al. | |
| 6,726,691 B2 | 4/2004 | Osorio et al. | |
| 6,730,124 B2 | 5/2004 | Steiner | |
| 6,746,451 B2 | 6/2004 | Middleton et al. | |
| 6,767,369 B2 | 7/2004 | Boyer, II et al. | |
| 6,814,736 B2 | 11/2004 | Reiley et al. | |
| 6,827,720 B2 | 12/2004 | Leali | |
| 6,863,672 B2 | 3/2005 | Reiley et al. | |
| 6,863,899 B2 | 3/2005 | Koblish et al. | |
| 6,869,434 B2 | 3/2005 | Choi | |
| 6,875,212 B2 | 4/2005 | Shaolian et al. | |
| 6,887,246 B2 | 5/2005 | Bhatnagar et al. | |
| 6,899,719 B2 | 5/2005 | Reiley et al. | |
| 6,917,827 B2 | 7/2005 | Kienzle, III | |
| 6,918,916 B2 | 7/2005 | Gobel et al. | |
| 6,923,813 B2 | 8/2005 | Phillips | |
| 6,979,341 B2 | 12/2005 | Scribner et al. | |
| 6,981,981 B2 | 1/2006 | Reiley | |
| 7,001,431 B2 | 2/2006 | Bao et al. | |
| 7,029,477 B2 | 4/2006 | Grimm | |
| 7,063,701 B2 | 6/2006 | Michelson | |
| 7,063,702 B2 | 6/2006 | Michelson | |
| 7,087,082 B2 | 8/2006 | Paul et al. | |
| 7,094,239 B1 | 8/2006 | Michelson | |
| 7,115,146 B2 | 10/2006 | Boyer, II et al. | |
| 7,144,414 B2 | 12/2006 | Harvie et al. | |
| 7,153,305 B2 | 12/2006 | Johnson et al. | |
| 7,153,306 B2 | 12/2006 | Ralph et al. | |
| 7,153,307 B2 | 12/2006 | Scribner | |
| 7,155,306 B2 | 12/2006 | Haitin et al. | |
| 7,160,305 B2 | 1/2007 | Schmieding | |
| 7,192,431 B2 | 3/2007 | Hangody et al. | |
| 7,226,481 B2 | 6/2007 | Kuslich | |
| 7,241,303 B2 | 7/2007 | Reiss et al. | |
| 7,250,055 B1 | 7/2007 | Vanderwalle | |
| 7,252,671 B2 | 8/2007 | Scribner et al. | |
| 7,261,716 B2 | 8/2007 | Strobel et al. | |
| 7,261,720 B2 | 8/2007 | Stevens et al. | |
| 7,313,430 B2 | 12/2007 | Urquhart et al. | |
| 7,399,306 B2 | 7/2008 | Reiley et al. | |
| 7,410,947 B2 | 8/2008 | Rueger et al. | |
| 7,448,264 B2 | 11/2008 | Boyce et al. | |
| 7,458,977 B2 | 12/2008 | McGinley et al. | |
| 7,468,075 B2 | 12/2008 | Lang et al. | |
| 7,476,226 B2 | 1/2009 | Weikel et al. | |
| 7,477,770 B2 | 1/2009 | Wehrli et al. | |
| 7,485,119 B2 | 2/2009 | Thelen et al. | |
| 7,488,348 B2 | 2/2009 | Truncale et al. | |
| 7,491,205 B1 | 2/2009 | Michelson | |
| 7,507,240 B2 * | 3/2009 | Olsen | A61B 17/6416 606/57 |
| 7,534,226 B2 | 5/2009 | Mernoe et al. | |
| 7,545,964 B2 | 6/2009 | Lang et al. | |
| 7,550,007 B2 | 6/2009 | Malinin | |
| 7,550,011 B2 | 6/2009 | Mckay et al. | |
| 7,556,295 B2 | 7/2009 | Holzheu | |
| 7,559,932 B2 | 7/2009 | Truckai et al. | |
| 7,575,578 B2 | 8/2009 | Wetzler et al. | |
| 7,594,917 B2 | 9/2009 | Whittaker et al. | |
| 7,608,097 B2 | 10/2009 | Kyle | |
| 7,608,098 B1 | 10/2009 | Stone | |
| 7,643,664 B2 | 1/2010 | Wehrli et al. | |
| 7,682,378 B2 | 3/2010 | Truckai et al. | |
| 7,704,256 B2 | 4/2010 | Sand et al. | |
| 7,708,742 B2 | 5/2010 | Scribner et al. | |
| 7,713,273 B2 | 5/2010 | Krueer et al. | |
| 7,731,720 B2 | 6/2010 | Sand et al. | |
| 7,753,963 B2 | 7/2010 | Boyer, II et al. | |
| 7,769,213 B2 | 8/2010 | Gregory et al. | |
| 7,771,431 B2 | 8/2010 | Scribner et al. | |
| 7,789,912 B2 | 9/2010 | Manzi et al. | |
| 7,811,290 B2 | 10/2010 | Rabiner | |
| 7,837,733 B2 | 11/2010 | Collins et al. | |
| 7,837,740 B2 | 11/2010 | Semler et al. | |

(56) References Cited

U.S. PATENT DOCUMENTS

| | | |
|---|---|---|
| 7,840,247 B2 | 11/2010 | Liew et al. |
| 7,846,206 B2 | 12/2010 | Oglaza et al. |
| 7,879,038 B2 | 2/2011 | Reiley et al. |
| 7,879,099 B2 | 2/2011 | Zipnick |
| 7,887,543 B2 | 2/2011 | Sand et al. |
| 7,887,546 B2 | 2/2011 | Gil |
| 7,896,885 B2 | 3/2011 | Miniaci et al. |
| 7,901,408 B2 | 3/2011 | Ek |
| 7,901,457 B2 | 3/2011 | Truncale et al. |
| 7,905,924 B2 | 3/2011 | White |
| 7,914,539 B2 | 3/2011 | Stone et al. |
| 7,927,339 B2 | 4/2011 | Ralph et al. |
| 7,931,840 B2 | 4/2011 | Michelson |
| 7,938,835 B2 | 5/2011 | Boucher et al. |
| 7,959,638 B2 | 6/2011 | Osorio et al. |
| 7,985,231 B2 | 7/2011 | Sankaran |
| 8,029,511 B2 | 10/2011 | Bowman et al. |
| 8,062,364 B1 | 11/2011 | Sharkey et al. |
| 8,070,753 B2 | 12/2011 | Truckai et al. |
| 8,092,480 B2 | 1/2012 | Layne |
| 8,133,226 B2 | 3/2012 | Chou et al. |
| 8,142,462 B2 | 3/2012 | Middleton |
| 8,152,813 B2 | 4/2012 | Osorio et al. |
| 8,168,692 B2 | 5/2012 | Wenz |
| 8,187,327 B2 | 5/2012 | Edidin et al. |
| 8,246,681 B2 | 8/2012 | Osorio et al. |
| 8,608,802 B2 | 12/2013 | Bagga et al. |
| 8,617,166 B2 | 12/2013 | Hanson et al. |
| 8,617,176 B2 | 12/2013 | Lizardi et al. |
| 8,636,745 B2 | 1/2014 | Almutairi et al. |
| 8,801,800 B2 | 8/2014 | Bagga et al. |
| 8,821,504 B2 | 9/2014 | Sharkey et al. |
| 8,864,768 B2 | 10/2014 | Hanson et al. |
| 8,906,032 B2 | 12/2014 | Hanson et al. |
| 8,951,261 B2 | 2/2015 | Sharkey et al. |
| 9,033,987 B2 | 5/2015 | Hanson et al. |
| 2002/0029084 A1 | 3/2002 | Paul et al. |
| 2002/0151897 A1 | 10/2002 | Zirkie, Jr. |
| 2003/0009235 A1 | 1/2003 | Manrique et al. |
| 2003/0097135 A1 | 5/2003 | Penenberg |
| 2003/0105468 A1 | 6/2003 | Gorek |
| 2003/0138473 A1 | 7/2003 | Koblish et al. |
| 2003/0220651 A1 | 11/2003 | Pusnik et al. |
| 2003/0225456 A1 | 12/2003 | Ek |
| 2004/0002759 A1 | 1/2004 | Ferree |
| 2004/0010261 A1 | 1/2004 | Hoag et al. |
| 2004/0106925 A1 | 6/2004 | Culbert |
| 2004/0127987 A1 | 7/2004 | Evans et al. |
| 2004/0167538 A1 | 8/2004 | Gerber et al. |
| 2005/0075641 A1 | 4/2005 | Singhatat et al. |
| 2005/0119219 A1 | 6/2005 | Bellini et al. |
| 2005/0119753 A1 | 6/2005 | McGahan et al. |
| 2005/0149022 A1 | 7/2005 | Shaolian et al. |
| 2005/0159812 A1 | 7/2005 | Dinger, III et al. |
| 2005/0177171 A1 | 8/2005 | Wetzler et al. |
| 2005/0182418 A1 | 8/2005 | Boyd et al. |
| 2005/0203622 A1 | 9/2005 | Steiner et al. |
| 2005/0203623 A1 | 9/2005 | Steiner et al. |
| 2005/0256527 A1 | 11/2005 | Delfosse et al. |
| 2005/0267584 A1 | 12/2005 | Burdulis, Jr. et al. |
| 2005/0288795 A1 | 12/2005 | Bagga et al. |
| 2006/0052791 A1 | 3/2006 | Hagen et al. |
| 2006/0064164 A1 | 3/2006 | Thelen et al. |
| 2006/0084986 A1 | 4/2006 | Grinberg et al. |
| 2006/0247642 A1 | 11/2006 | Stone et al. |
| 2006/0271059 A1 | 11/2006 | Reay-Young et al. |
| 2007/0055280 A1 | 3/2007 | Osorio et al. |
| 2007/0100462 A1 | 5/2007 | Lang et al. |
| 2007/0127987 A1 | 6/2007 | Altenbuchner |
| 2007/0276370 A1 | 11/2007 | Altarac et al. |
| 2007/0282346 A1 | 12/2007 | Scribner et al. |
| 2008/0027434 A1 | 1/2008 | Zucherman et al. |
| 2008/0039857 A1 | 2/2008 | Giersch et al. |
| 2008/0039866 A1 | 2/2008 | Stetz et al. |
| 2008/0103506 A1 | 5/2008 | Volpi et al. |
| 2008/0195115 A1 | 8/2008 | Oren et al. |
| 2008/0243127 A1 | 10/2008 | Lang et al. |
| 2008/0281331 A1 | 11/2008 | Fritzinger et al. |
| 2008/0288006 A1 | 11/2008 | Brannon |
| 2008/0306490 A1 | 12/2008 | Lakin et al. |
| 2009/0062797 A1 | 3/2009 | Huebner et al. |
| 2009/0069901 A1 | 3/2009 | Truncale et al. |
| 2009/0093813 A1 | 4/2009 | Elghazaly et al. |
| 2009/0204158 A1 | 8/2009 | Sweeney |
| 2010/0015202 A1 | 1/2010 | Semler et al. |
| 2010/0076503 A1 | 3/2010 | Beyar et al. |
| 2010/0145451 A1 | 6/2010 | Dee |
| 2010/0179549 A1 | 7/2010 | Keller et al. |
| 2010/0274254 A1 | 10/2010 | Boileau et al. |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125160 A1 | 5/2011 | Bagga et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2014/0107781 A1 | 4/2014 | Bagga et al. |
| 2014/0114369 A1 | 4/2014 | Hanson et al. |
| 2014/0350683 A1 | 11/2014 | Sharkey et al. |
| 2014/0350685 A1 | 11/2014 | Bagga et al. |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| EP | 2501303 A1 | 9/2012 |
| EP | 2501306 A1 | 9/2012 |
| EP | 2501314 A1 | 9/2012 |
| EP | 2501342 A1 | 9/2012 |
| WO | WO-03084412 A1 | 10/2003 |
| WO | WO-2005079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

"U.S. Appl. No. 12/950,230, Examiner Interview Summary mailed Nov. 12, 2014", 3 pgs.

"U.S. Appl. No. 12/950,230, Response filed Nov. 2, 2012 to Non Final Office Action mailed Aug. 2, 2012", 8 pgs.

"U.S. Appl. No. 12/950,230, Response filed Nov. 17, 2014 to Non-Final Office Action mailed Jul. 17, 2014", 15 pgs.

"U.S. Appl. No. 12/950,273, Response filed Oct. 24, 2014 to Non-Final Office Action mailed Apr. 25, 2014", 14 pgs.

"U.S. Appl. No. 12/950,355, Notice of Allowance mailed Dec. 9, 2014", 6 pgs.

"U.S. Appl. No. 12/950,355, Response filed Oct. 28, 2014 to Non-Final Office Action mailed Jul. 29, 2014", 21 pgs.

"U.S. Appl. No. 14/143,883, Response filed Dec. 4, 2014 to Non-Final Office Action mailed Aug. 4, 2014", 9 pgs.

"U.S. Appl. No. 14/453,301, Preliminary Amendment filed Oct. 6, 2014", 8 pgs.

"Chinese Application Serial No. 201080052580.9, Office Action mailed Nov. 25, 2014", (W/English Translation), 18 pgs.

"Chinese Application Serial No. 201080052583.2, Response filed Sep. 26, 2014 to Office Action mailed Mar. 14, 2014", (W/English Translation of Claims), 10 pgs.

"U.S. Appl. No. 12/950,230, Final Office Action mailed Jan. 13, 2015", 10 pgs.

"U.S. Appl. No. 12/950,230, Non Final Office Action mailed Apr. 15, 2015", 10 pgs.

"U.S. Appl. No. 12/950,230, Response filed Mar. 24, 2015 to Final Office Action mailed Jan. 13, 2015", 11 pgs.

(56) References Cited

OTHER PUBLICATIONS

"U.S. Appl. No. 12/950,273, Advisory Action mailed May 12, 2015", 3 pgs.
"U.S. Appl. No. 12/950,273, Final Office Action mailed Feb. 4, 2015", 28 pgs.
"U.S. Appl. No. 12/950,273, Response filed May 4, 2015 to Final Office Action mailed Feb. 4, 2015", 14 pgs.
"U.S. Appl. No. 12/950,273, Response filed Jun. 4, 2015 to Final Office Action mailed Feb. 4, 2015", 14 pgs.
"U.S. Appl. No. 14/109,368, Non Final Office Action mailed Mar. 11, 2015", 6 pgs.
"U.S. Appl. No. 14/109,368, Response filed May 26, 2015 to Non-Final Office Action mailed Mar. 11, 2015", 12 pgs.
"U.S. Appl. No. 14/143,883, Notice of Allowance mailed Jan. 26, 2015", 6 pgs.
"U.S. Appl. No. 14/454,298, Notice of Allowance mailed Mar. 17, 2015", 8 pgs.
"U.S. Appl. No. 14/617,058, Preliminary Amendment filed Feb. 18, 2015", 8 pgs.
"U.S. Appl. No. 14/695,516, Preliminary Amendment filed May 27, 2015", 6 pgs.
"Australian Application Serial No. 2010321745, Office Action mailed Jan. 12, 2015", 3 pgs.
"Australian Application Serial No. 2010321745, Response filed Apr. 24, 2015 to Office Action mailed Jan. 12, 2015", (18 pgs).
"Australian Application Serial No. 2010321812, Office Action mailed Jan. 12, 2015", 3 pgs.
"Australian Application Serial No. 2010321812, Response filed Apr. 24, 2015 to Office Action mailed Jan. 12, 2015", 19 pgs.
"Chinese Application Serial No. 201080052569.2 Response filed Nov. 7, 2014 to Non Final Office Action mailed Jun. 10, 2014", (W/ English Translation), 12 pgs.
"Chinese Application Serial No. 201080052569.2, Office Action mailed Jan. 28, 2015", (W/ English Translation), 5 pgs.
"Chinese Application Serial No. 201080052569.2, Response filed Mar. 26, 2015 to Office Action mailed Jan. 28, 2015", W/ English Claims, 10 pgs.
"Chinese Application Serial No. 201080052578.1, Office Action mailed Dec. 17, 2014", (W/ English Translation), 4 pgs.
"Chinese Application Serial No. 201080052578.1, Response filed Jan. 22, 2015 to Office Action mailed Dec. 17, 2014", (W/ English Translation), 8 pgs.
"Chinese Application Serial No. 201080052578.1, Response filed Aug. 12, 2014 to Office Action mailed Apr. 1, 2014", W/ English Claims, 13 pgs.
"Chinese Application Serial No. 201080052580.9, Response filed Aug. 14, 2014 to Office Action mailed Apr. 3, 2014", W/ English Claims, 12 pgs.
"Chinese Application Serial No. 201080052583.2, Office Action mailed Dec. 24, 2014", (W/ English Translation), 4 pgs.
"U.S. Appl. No. 12/950,061, Final Office Action mailed Jul. 15, 2013", 7 pgs.
"U.S. Appl. No. 12/950,061, Non Final Office Action mailed Feb. 7, 2013", 7 pgs.
"U.S. Appl. No. 12/950,061, Notice of Allowance mailed Oct. 1, 2013", 6 pgs.
"U.S. Appl. No. 12/950,061, Preliminary Amendment filed Feb. 8, 2011", 3 pgs.
"U.S. Appl. No. 12/950,061, Response filed Jun. 7, 2013 to Non Final Office Action mailed Feb. 7, 2013", 14 pgs.
"U.S. Appl. No. 12/950,061, Response filed Sep. 16, 2013 to Final Office Action mailed Jul. 15, 2013", 13 pgs.
"U.S. Appl. No. 12/950,097, Final Office Action mailed Dec. 10, 2013", 6 pgs.
"U.S. Appl. No. 12/950,097, Non Final Office Action mailed Feb. 15, 2013", 8 pgs.
"U.S. Appl. No. 12/950,097, Non Final Office Action mailed Aug. 6, 2013", 6 pgs.
"U.S. Appl. No. 12/950,097, Notice of Allowance mailed Apr. 2, 2014", 5 pgs.
"U.S. Appl. No. 12/950,097, Notice of Allowance mailed Jul. 9, 2014", 5 pgs.
"U.S. Appl. No. 12/950,097, Preliminary Amendment filed Feb. 7, 2011", 3 pgs.
"U.S. Appl. No. 12/950,097, Response filed Mar. 10, 2014 to Final Office Action mailed Dec. 10, 2013", 13 pgs.
"U.S. Appl. No. 12/950,097, Response filed Jun. 17, 2013 to Non Final Office Action mailed Feb. 15, 2013", 15 pgs.
"U.S. Appl. No. 12/950,097, Response filed Nov. 6, 2013 to Non Final Office Action mailed Aug. 6, 2013", 14 pgs.
"U.S. Appl. No. 12/950,114, Final Office Action mailed Jul. 15, 2013", 6 pgs.
"U.S. Appl. No. 12/950,114, Non Final Office Action mailed Feb. 6, 2014", 6 pgs.
"U.S. Appl. No. 12/950,114, Non Final Office Action mailed Mar. 7, 2013", 6 pgs.
"U.S. Appl. No. 12/950,114, Notice of Allowance mailed Jun. 16, 2014", 5 pgs.
"U.S. Appl. No. 12/950,114, Preliminary Amendment filed Feb. 8, 2011", 3 pgs.
"U.S. Appl. No. 12/950,114, Response filed May 6, 2014 to Non-Final Office Action mailed Feb. 6, 2014", 7 pgs.
"U.S. Appl. No. 12/950,114, Response filed Jun. 7, 2013 to Non Final Office Action mailed Mar. 7, 2013", 8 pgs.
"U.S. Appl. No. 12/950,114, Response filed Sep. 16, 2013 to Final Office Action mailed Jul. 15, 2013", 8 pgs.
"U.S. Appl. No. 12/950,154, Examiner Interview Summary mailed Aug. 19, 2014", 3 pgs.
"U.S. Appl. No. 12/950,154, Final Office Action mailed Aug. 8, 2013", 7 pgs.
"U.S. Appl. No. 12/950,154, Non Final Office Action mailed Feb. 25, 2014", 6 pgs.
"U.S. Appl. No. 12/950,154, Non Final Office Action mailed Mar. 15, 2013", 8 pgs.
"U.S. Appl. No. 12/950,154, Preliminary Amendment filed Feb. 7, 2011", 4 pgs.
"U.S. Appl. No. 12/950,154, Response filed Jun. 17, 2013 to Non Final Office Action mailed Mar. 15, 2013", 15 pgs.
"U.S. Appl. No. 12/950,154, Response filed Aug. 25, 2014 to Non-Final Office Action mailed Feb. 25, 2014", 18 pgs.
"U.S. Appl. No. 12/950,154, Response filed Oct. 8, 2013 to Final Office Action mailed Aug. 8, 2013", 18 pgs.
"U.S. Appl. No. 12/950,183, Examiner Interview Summary mailed Feb. 13, 2014", 3 pgs.
"U.S. Appl. No. 12/950,183, Final Office Action mailed Oct. 30, 2012", 16 pgs.
"U.S. Appl. No. 12/950,183, Non Final Office Action mailed May 29, 2012", 10 pgs.
"U.S. Appl. No. 12/950,183, Non Final Office Action mailed Oct. 11, 2013", 12 pgs.
"U.S. Appl. No. 12/950,183, Notice of Allowance mailed Feb. 19, 2014", 5 pgs.
"U.S. Appl. No. 12/950,183, Notice of Allowance mailed Jun. 6, 2014", 7 pgs.
"Application U.S. Appl. No. 12/950,183, Preliminary Amendment filed Feb. 8, 2011", 4 pgs.
"Application U.S. Appl. No. 12/950,183, Response filed Jan. 13, 2014 to Non Final Office Action mailed Oct. 11, 2013", 11 pgs.
"U.S. Appl. No. 12/950,183, Response filed Apr. 30, 2013 to Final Office Action mailed Oct. 30, 2012", 11 pgs.
"U.S. Appl. No. 12/950,183, Response filed May 11, 2012 to Restriction Requirement mailed Apr. 13, 2012", 2 pgs.
"U.S. Appl. No. 12/950,183, Response filed Aug. 28, 2012 to Non Final Office Action mailed May 29, 2012", 10 pgs.
"U.S. Appl. No. 12/950,183, Restriction Requirement mailed Apr. 13, 2012", 8 pgs.
"U.S. Appl. No. 12/950,183, Supplemental Amendment filed Feb. 7, 2014", 8 pgs.
"U.S. Appl. No. 12/950,230, Final Office Action mailed Jan. 11, 2013", 10 pgs.
"U.S. Appl. No. 12/950,230, Non Final Office Action mailed Jul. 17, 2014", 10 pgs.

(56) References Cited

OTHER PUBLICATIONS

"U.S. Appl. No. 12/950,230, Non Final Office Action mailed Aug. 2, 2012", 9 pgs.
"U.S. Appl. No. 12/950,230, Preliminary Amendment filed Feb. 8, 2011", 3 pgs.
"U.S. Appl. No. 12/950,230, Response filed Apr. 11, 2013 to Final Office Action mailed Jan. 11, 2013", 10 pgs.
"U.S. Appl. No. 12/950,273, Final Office Action mailed Nov. 6, 2012", 9 pgs.
"U.S. Appl. No. 12/950,273, Non Final Office Action mailed Apr. 13, 2012", 15 pgs.
"U.S. Appl. No. 12/950,273, Non Final Office Action mailed Apr. 25, 2014", 12 pgs.
"U.S. Appl. No. 12/950,273, Preliminary Amendment filed Feb. 8, 2011", 3 pgs.
"U.S. Appl. No. 12/950,273, Response filed Mar. 6, 2013 to Final Office Action mailed Nov. 6, 2012", 10 pgs.
"U.S. Appl. No. 12/950,273, Response filed Jul. 12, 2012 to Non Final Office Action mailed Apr. 13, 2012", 12 pgs.
"U.S. Appl. No. 12/950,306, Final Office Action mailed Nov. 26, 2012", 9 pgs.
"U.S. Appl. No. 12/950,306, Non Final Office Action mailed Jun. 14, 2012", 11 pgs.
"U.S. Appl. No. 12/950,306, Notice of Allowance mailed May 28, 2013", 9 pgs.
"U.S. Appl. No. 12/950,306, Notice of Allowance mailed Aug. 13, 2013", 9 pgs.
"U.S. Appl. No. 12/950,306, Preliminary Amendment filed Feb. 8, 2011", 7 pgs.
"U.S. Appl. No. 12/950,306, Response filed Apr. 30, 2013 to Final Office Action mailed Nov. 26, 2012", 15 pgs.
"U.S. Appl. No. 12/950,306, Response filed Sep. 13, 2012 to Non Final Office Action mailed Jun. 14, 2012", 11 pgs.
"U.S. Appl. No. 12/950,355, Final Office Action mailed Mar. 12, 2013", 15 pgs.
"U.S. Appl. No. 12/950,355, Non Final Office Action mailed Jul. 29, 2014", 9 pgs.
"U.S. Appl. No. 12/950,355, Non Final Office Action mailed Aug. 13, 2012", 16 pgs.
"U.S. Appl. No. 12/950,355, Response filed Jan. 14, 2013 to Non Final Office Action mailed Aug. 13, 2012", 17 pgs.
"U.S. Appl. No. 12/950,355, Response filed Jul. 12, 2013 to Final Office Action mailed Mar. 12, 2013", 20 pgs.
"U.S. Appl. No. 14/143,883, Non Final Office Action mailed Aug. 4, 2014", 6 pgs.
"U.S. Appl. No. 14/454,298, Preliminary Amendment filed Sep. 18, 2014", 7 pgs.
"Chinese Application Serial No. 201080020717.2, Office Action mailed Jan. 9, 2014", (W/English Translation), 11 pgs.
"Chinese Application U.S. Appl. No. 201080052569.2, Office Action mailed Apr. 25, 2014", w/English Translation, 17 pgs.
"Chinese Application Serial No. 201080052578.1, Office Action mailed Apr. 1, 2014", w/English Translation, 11 pgs.
"Chinese Application Serial No. 201080052580.9, Office Action mailed Apr. 3, 2014", w/English Translation, 18 pgs.
"Chinese Application Serial No. 201080052583.2, Office Action mailed Mar. 14, 2014", w/English Translation, 9 pgs.
"European Application Serial No. 10832277.7, Office Action mailed Jun. 27, 2012", 2 pgs.
"European Application Serial. No. 10832285.0, Office Action mailed Jun. 27, 2012", 2 pgs.
"International Application Serial No. PCT/US2010/057426, International Preliminary Report on Patentability mailed May 22, 2012", 9 pgs.
"International Application Serial No. PCT/US2010/057426, International Search Report and Written Opinion mailed Jan. 24, 2011", 10 pgs.
"International Application Serial No. PCT/US2010/057440, International Preliminary Report on Patentability mailed May 22, 2012", 7 pgs.
"International Application Serial No. PCT/US2010/057440, International Search Report and Written Opinion mailed Feb. 7, 2011", 8 pgs.
"International Application Serial No. PCT/US2010/057456, International Preliminary Report on Patentability mailed May 22, 2012", 6 pgs.
"International Application Serial No. PCT/US2010/057456, International Search Report and Written Opinion mailed Jan. 14, 2011", 7 pgs.
"International Application Serial No. PCT/US2010/057471, International Preliminary Report on Patentability mailed May 31, 2012", 7 pgs.
"International Application Serial No. PCT/US2010/057471, International Search Report mailed Jan. 18, 2011", 2 pgs.
"International Application Serial No. PCT/US2010/057471, Written Opinion mailed Jan. 18, 2011", 5 pgs.
"International Application Serial No. PCT/US2010/057475, International Preliminary Report on Patentability mailed May 22, 2012", 6 pgs.
"International Application Serial No. PCT/US2010/057475, International Search Report mailed Jan. 18, 2011", 8 pgs.
"International Application Serial No. PCT/US2010/057475, Written Opinion mailed Jan. 18, 2011", 5 pgs.
"International Application Serial No. PCT/US2010/057483, International Preliminary Report on Patentability mailed May 22, 2012", 6 pgs.
"International Application Serial No. PCT/US2010/057483, International Search Report and Written Opinion mailed Feb. 2, 2011", 7 pgs.
"International Application Serial No. PCT/US2010/057498, International Preliminary Report on Patentability mailed May 22, 2012", 5 pgs.
"International Application Serial No. PCT/US2010/057498, International Search Report mailed Jan. 24, 2011", 2 pgs.
"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; a guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.
"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

\* cited by examiner

COORDINATE MAPPING SYSTEM FOR JOINT TREATMENT

CROSS-REFERENCE TO RELATED APPLICATIONS

This application is a continuation of U.S. patent application Ser. No. 12/950,114 filed Nov. 19, 2010, and entitled "COORDINATE MAPPING SYSTEM FOR JOINT TREATMENT," which claims priority to U.S. Provisional No. 61/311,632, filed Mar. 8, 2010, and entitled "COORDINATE MAPPING SYSTEM FOR KNEE JOINT REPAIR AND METHODS OF USE," and U.S. Provisional No. 61/263,170 filed Nov. 20, 2009, and entitled "METHOD FOR TREATING JOINT PAIN AND ASSOCIATED INSTRUMENTS," all of which are herein incorporated by reference in their entirety.

This application also related to co-pending and co-owned U.S. patent application Ser. No. 12/950,355, filed Nov. 19, 2010 and entitled "SUBCHONDRAL TREATMENT OF JOINT PAIN," the content of which is herein incorporated in its entirety by reference.

FIELD

The present invention relates to devices and tools for surgical treatment of joints, and more particularly to instruments and associated methods for the surgical repair and treatment of bone tissue at these joints. Even more particularly, the present invention relates to a coordinate mapping system for locating a bone defect using anatomical landmarks.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

In current practice, surgeons typically "eyeball" the target site on a bone to be repaired. Most conventional targeting and location methods are crude and provide little guidance to a surgeon during the actual surgical procedure. Accordingly, it would be desirable to provide methods and systems in which a bone defect can be accurately located and provide a reference framework that can be used in a surgical procedure irrespective of the approach.

SUMMARY

The present disclosure relates to a coordinate mapping system for locating a bone defect using anatomical landmarks. The system allows the surgeon to accurately locate the bone defect with a reference framework and access the defect using a positioning instrument during surgery.

In one exemplary embodiment, a coordinate mapping system is provided for locating a defect in a bone. The system comprises a positioning instrument for controlled delivery of a device to a target site, the instrument comprising a main body and a rail extending from the main body, the rail including a series of indicia corresponding to predefined grid lines, and a template configured to overlay an image of a bone having a defect at the target site. The template can include a predefined grid for determining a set of coordinates to locate the target site using the positioning instrument. The grid may be, for exampled, a radial grid.

In another exemplary embodiment, a method of accessing a target site near a defect on a bone is provided. The method comprises the step of providing a template having a predefined grid for determining a set of coordinates to locate a target site on a bone having a defect, overlaying the template on an image of the bone, the template being aligned with an anatomical landmark on the bone, determining a set of coordinates of the location of the defect from the grid, providing a positioning instrument for controlled delivery of a device to the target site, comprising a main body and a rail extending from the main body, the rail including a series of indicia corresponding to predefined grid lines on the template, aligning the positioning instrument to the anatomical landmark on the bone so that the indicia on the positioning instrument are consistent with the grid of the template, and accessing the target site using the set of coordinates.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1A:
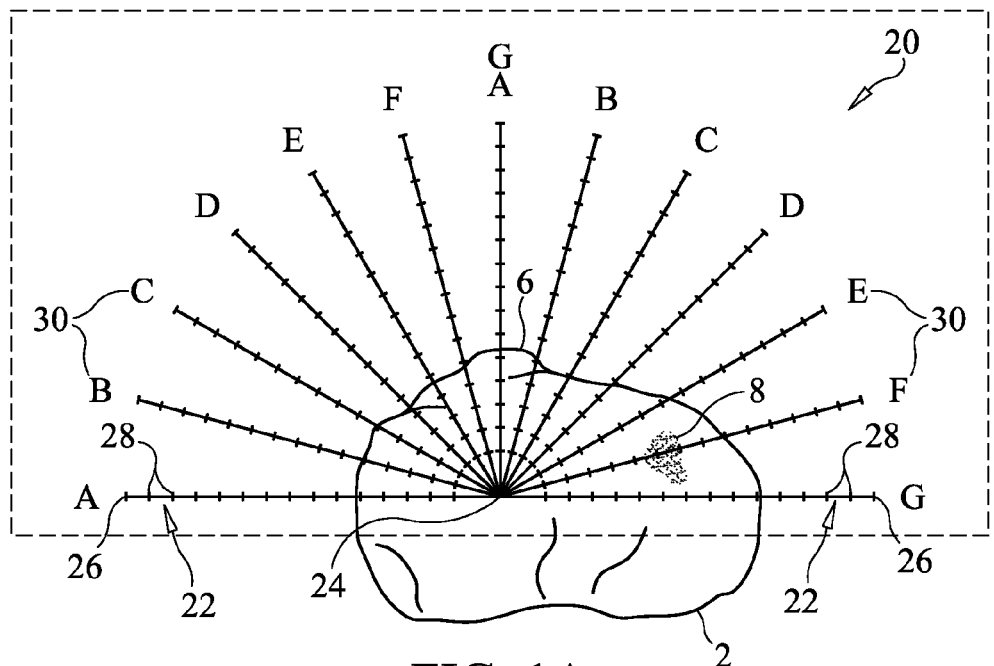
FIGS. 1A and 1B show an exemplary embodiment of a radial coordinate template superimposed over a top-down image of a bone, such as the tibia, having a defect.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression of defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affects bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatments can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) of calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesions.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heal stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture of stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or ostengenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

It is to be understood that both the foregoing general description and the following detailed description are exemplary and explanatory only and are not restrictive of the disclosure. Additional features of the disclosure will be set forth in part in the description which follows or may be learned by practice of the disclosure.

Figure 1B:
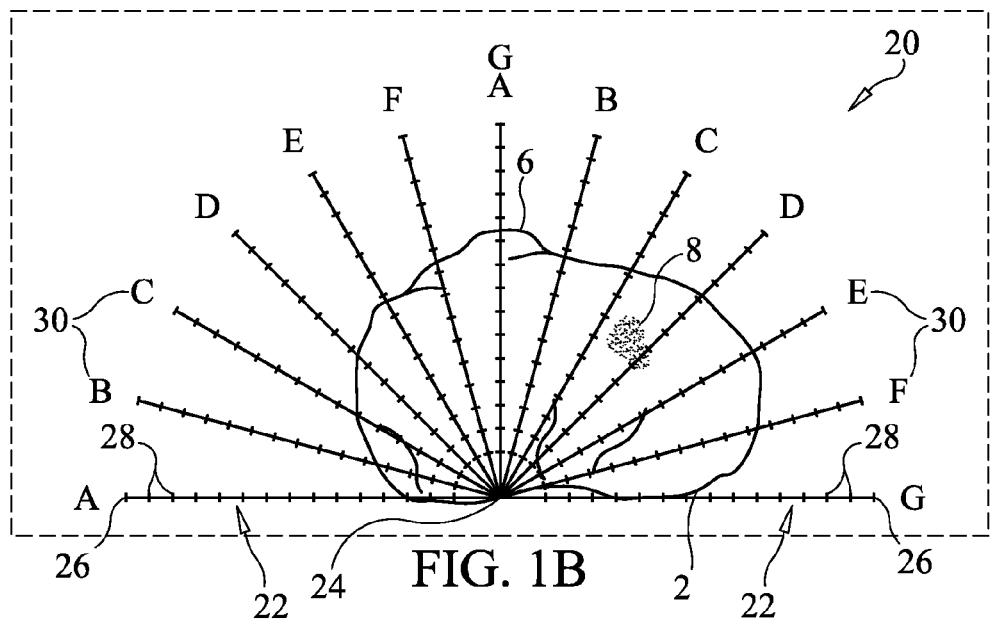

Referring now to FIGS. 1A and 1B, embodiments of the present disclosure employ a coordinate mapping system 10 comprising a template 20 and a positioning instrument 100. In the present examples, the template 20 may include radial coordinates having a radial component and an angular component. This coordinate mapping system 10 may be use to locate a bone defect with the positioning instrument 100. The coordinate mapping system 10 more naturally resembles the various approaches that may be employed by a surgeon.

In one embodiment, the template 20 utilizes a predefined radial grid that corresponds to indicia 30 for keyed angles on the positioning instrument 100. The template may be implemented in tangible form, such as a transparency, that may be placed over an image of the bone to be treated. The image could be for example, an MRI, an X-ray, other scanned image, or a combination of one or more of these images. Alternatively, the template 20 may be implemented using software that displays the predefined grid as an overlay onto a display of the image. The template 20 may be customized to account for variations in the dimensions and angle of the image.

While the present examples of templates 20 employ a radial grid, it is understood that other types of grids and coordinate systems may be employed with the template 20 of the present disclosure. Another type of grid may include a Cartesian grid, for instance. Further, any combination of grids or coordinate systems may be utilized in combination together with the present system 10 for even more precise location of the bone defect.

FIGS. 1A and 1B show an exemplary embodiment of a template 20 of the coordinate mapping system 10 superimposed over an image of a bone, such as the tibia 2, having a defect 8. As shown, the template 20 comprises a series of radial grid lines 22 spanning 180 degrees. The radial grid lines 22 extend from a common starting point at vertex 24, and terminate at an outer edge 26. Each radial grid line 22 includes a set of interval markings 28 designating a predetermined distance or length. In addition, the radial grid lines 22 are labeled by indicia 30.

As shown for one embodiment, the radial grid lines 22 may be distributed in 15 degree intervals. However, it is understood that the radial grid lines 22 may be separated by other degrees of intervals, such as 5, 10, 20, etc. degree intervals as appropriate for the surgical application of the system 10.

Interval markings 28 on each of the radial grid lines 22 may serve as a convenient indicator of distance from either the vertex 24 or the outer edge 26. The interval markings 28, for example, may represent a predetermined distance of 2, 5, or 10 mm, for example.

To implement the coordinate mapping system 10, the template 20 is positioned such that its vertical grid line G-A aligns with the tubercle 6 of tibia 2, as shown in FIGS. 1A and 1B. Depending on the desired approach angle (e.g., medial, lateral, etc.), the horizontal grid line A-G of template 20 may be adjusted up or down until the defect 8 falls within the desired coordinates represented by the angular position of the two most adjacent grid lines 22 as well as the interval markings 28 of the closest of the two grid lines 22. For example, in FIG. 1A the defect 8 can be located along grid line F, which provides a relatively shallow angle of approach. Alternatively, in FIG. 1B, the horizontal line A-G of the template 20 is moved down, and the same defect 8 can be located between grid lines C and D, which provides a relatively wider angle of approach.

Figure 2:
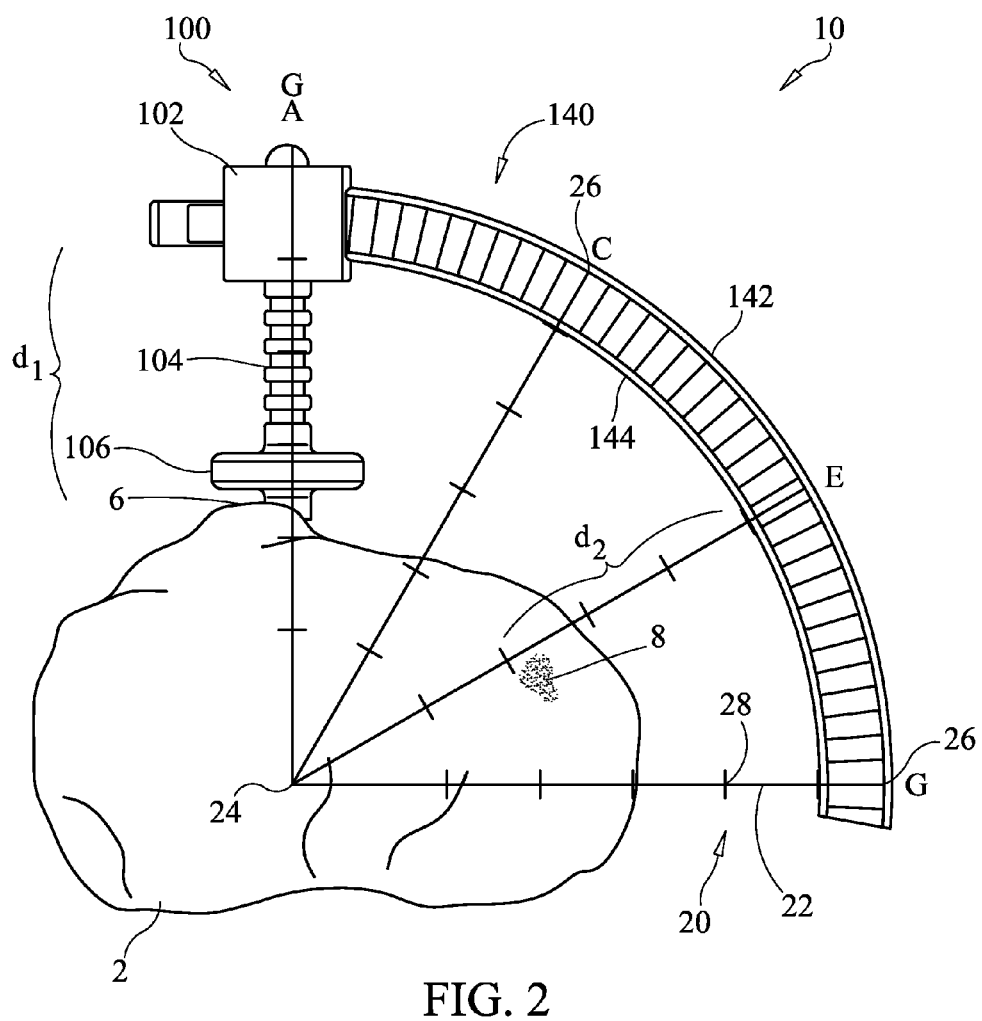
FIG. 2 conceptually illustrates the implementation of the radial coordinate template of FIGS. 1A and 1B by an exemplary embodiment of an positioning instrument of the present disclosure.

FIG. 2 conceptually illustrates the implementation of the template 20 of FIGS. 1A and 1B onto a positioning instrument 100 of the coordinate mapping system 10 of the present disclosure. For purposes of clarity, certain portions of the template 20 are not shown to allow more space for viewing. As can be seen, the positioning instrument 100 comprises a main body 102 from which extends an arm 104 that terminates at contact pad 106 configured to seat against tubercle 6. Of note, the vertical axis G-A of the template 20 is aligned with the central axis of arm 104. The positioning instrument 100 also includes a rail 140 that extends from the main body 102. As shown, the outer edge 26 of the template 20 matches the outer surface 142 of rail 140. In some embodiments, the outer edge 26 of the template 20 can be matched to the inner surface 144 of the rail 140.

In use, the template 20 provides a mechanism for determining a set of three coordinates for locating the defect 8 based on the patient's own anatomy (i.e., tubercle). For example, as shown in FIG. 2, the template 20 indicates a first coordinate, distance $d_1$, represented by the number of interval markings 28 between the outer edge 26 to tubercle 6 along vertical axis G-A. The second coordinate may represent the angular component corresponding to radial grid line 22 as indicated by the indicia labeled "E" in this example. The third coordinate may represent the distance $d_2$ represented by the number of interval markings 28 between the outer edge 26 to the location of the defect 8 along the "E" radial grid line 22. Accordingly, the example shown in FIG. 2 may have a coordinate set of 2-60-2.5.

Figure 3A:
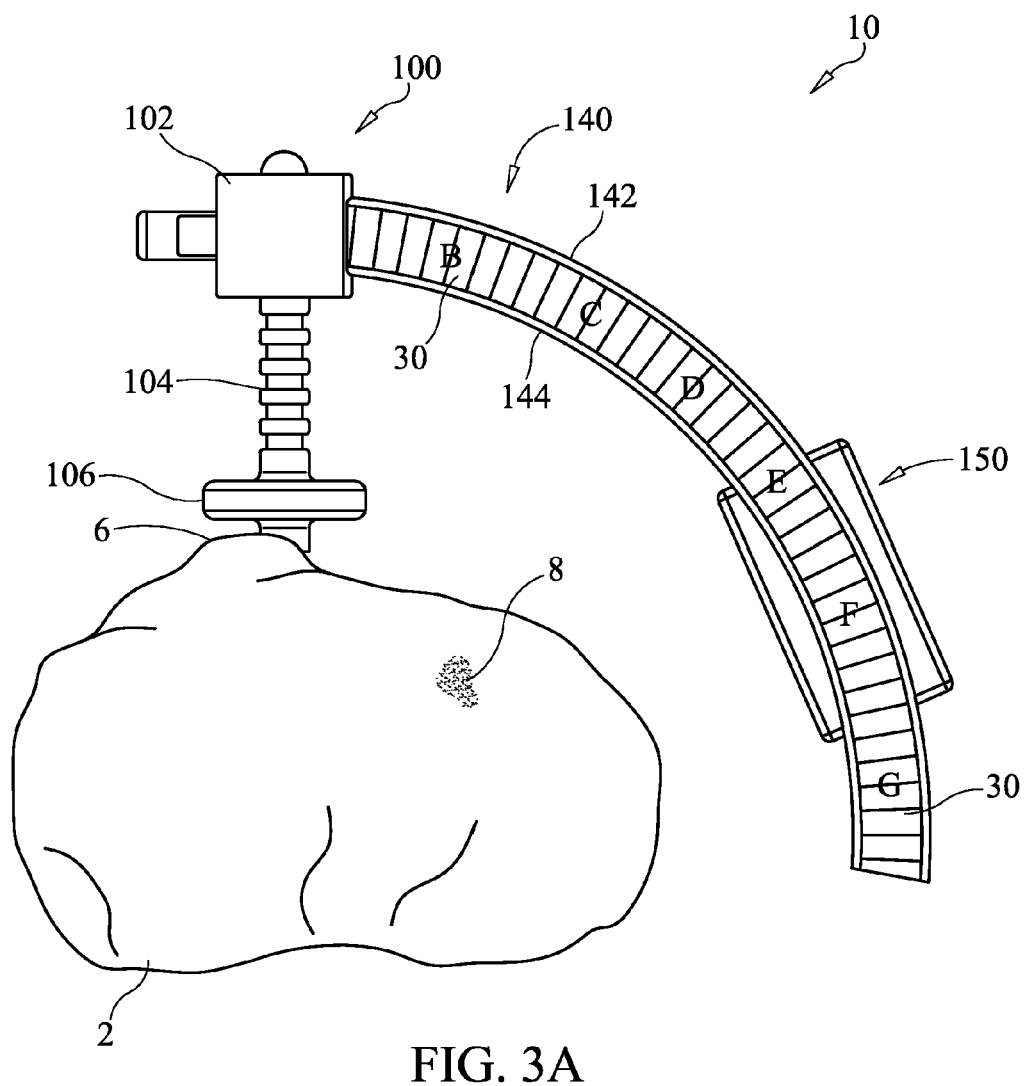
FIG. 3A shows a top-down view of an exemplary embodiment of an positioning instrument of the present disclosure.
Figure 3B:
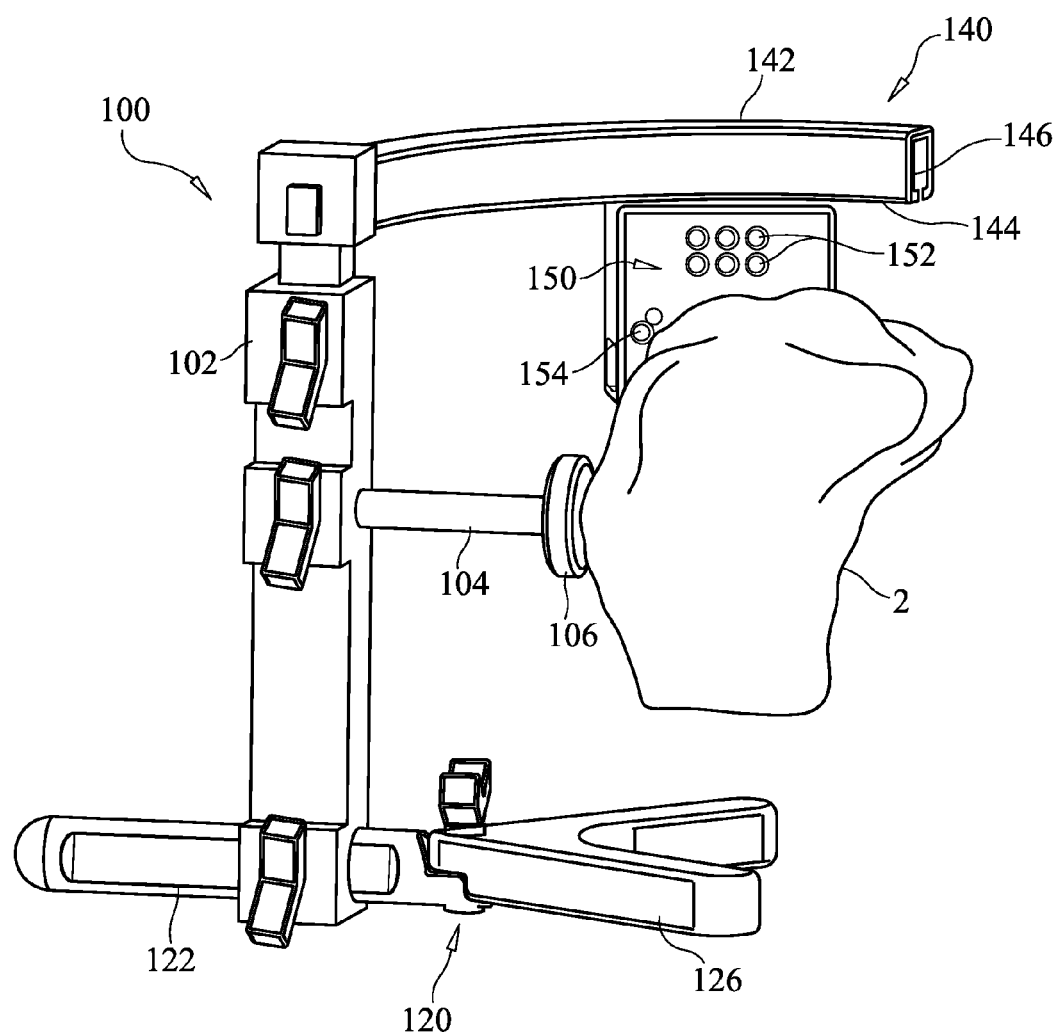
FIG. 3B shows a perspective side view of the positioning instrument of FIG. 3A.

FIGS. 3A and 3B illustrate in greater detail the positioning instrument 100 of coordinate mapping system 10. As shown in FIG. 3B, the positioning instrument 100 may further include a brace component 120. The brace component 120 may comprise a shaft 122 hinged to brace 126. The brace 126 may pivot relative to the shaft 122, which can also be adjusted relative to the main body 102 such that the brace can be adjusted to accommodate and bear against the patient's leg.

As also shown, the rail 140 may be circular. However, it is understood that the rail 140 may be configured with any other shape. The height of the rail 140 may be adjustable relative to the main body 102. In one embodiment, a pointer or indicator (not shown) could be provided that points to the joint from the vertically adjustable portion of the body 102 that can be visible with use of a C-arm during surgery. The surgeon would align the pointer with a C-arm visible landmark such as the joint line by adjusting the vertical location of the upper portion of the instrument 100.

Rail 140 may comprise an open slot 146 for receiving an alignment guide 150. Though not shown, the alignment guide 150 may have a protrusion or tab that allows it to seat within and slide inside the open slot 146. The alignment guide 150 may also include device portals 152 for receiving a device, as well as tool-receiving holes 154 for receiving a tool such as a pin 50, for example. The device portals 152 may be arranged parallel to each other. It is understood that these portals 152 may be provided in other arrangements such as in an arc pattern or these portals 152 may be angled to converge.

In one embodiment, the rail 140 may extend at an angle to a transverse plane of the tibia 2. The angle could be in the range of about 1 to 15 degrees, more preferably about 2 to 10 degrees, and even more preferably about 3 to 7 degrees. In one example, the rail 140 may be configured to extend at an angle of about 7 degrees to a transverse plane of the tibial plateau. This slight angle enables the rail 140 to be oriented parallel to the tibial plateau (which typically has a natural, inherent slope), thereby allowing the user to have instrumentation that better matches the natural contours of the bone to be treated and which allows for the correct angular access to the target site. Accordingly, the angular orientation of the rail 140 allows the user a greater angular opening to access the bone clear of ligament and other surrounding soft tissue, and prevents inadvertent angular insertion of any instruments or devices through cartilage or other unintended bone or soft tissue, causing damage to the joint.

Figure 4A:
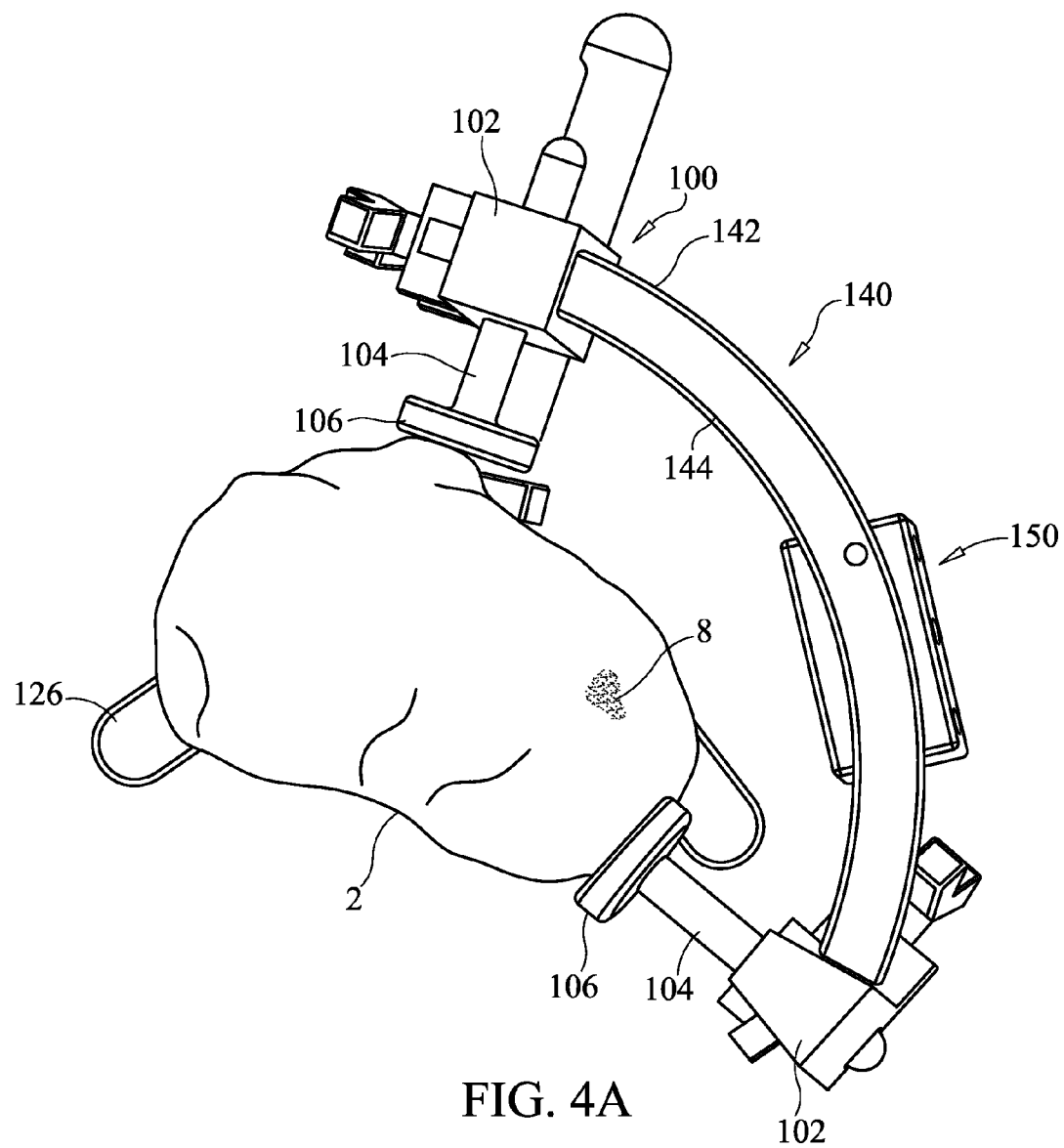
FIG. 4A shows a top-down view of another exemplary embodiment of an positioning instrument of the present disclosure.
Figure 4B:
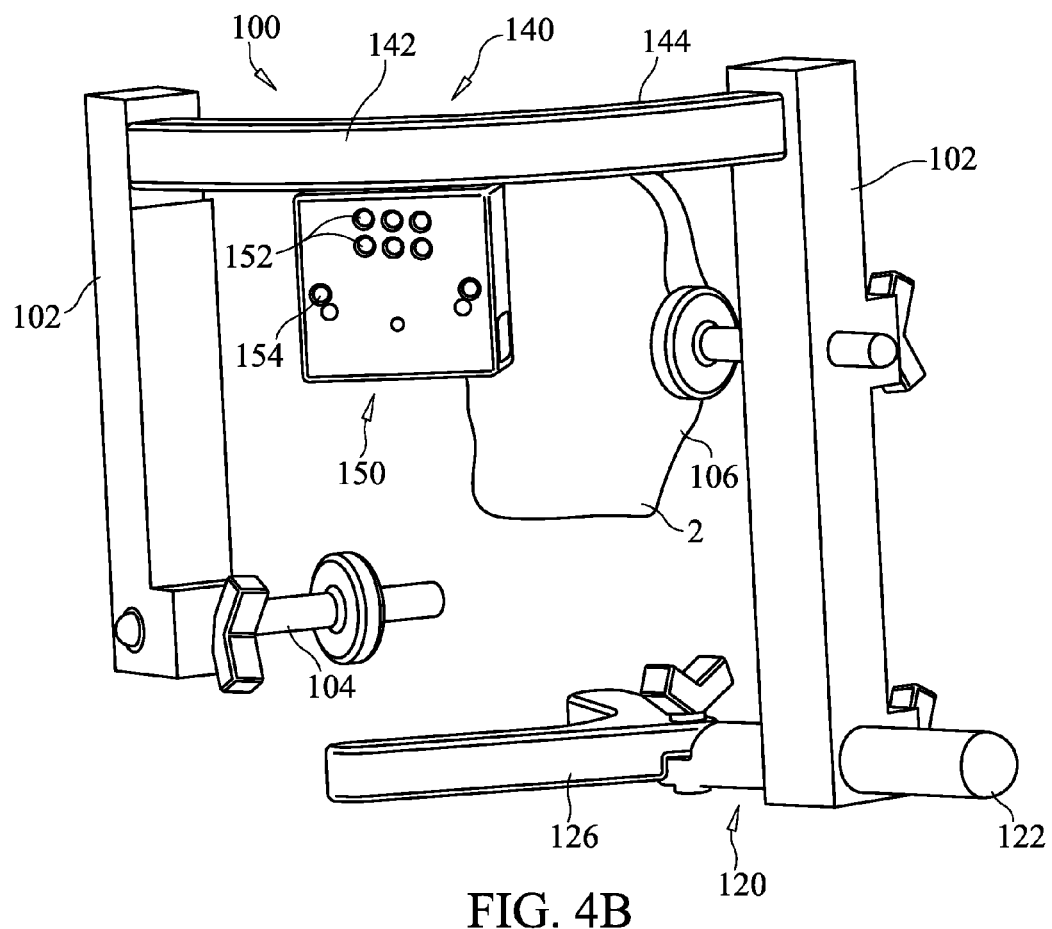
FIG. 4B shows a perspective side view of the positioning instrument of FIG. 4A.

FIGS. 4A and 4B illustrate another exemplary embodiment of a positioning instrument 100 whereby there are two main bodies 102 on either end of the rail 140, each main body 102 having an arm 104 with contact pad 106 for seating against the tibia 2. As further shown, the arms 104 may be configured to extend through the contact pads 106 and into the tibia 2 in order to secure the positioning instrument 100 to the bone.

Figure 5A:
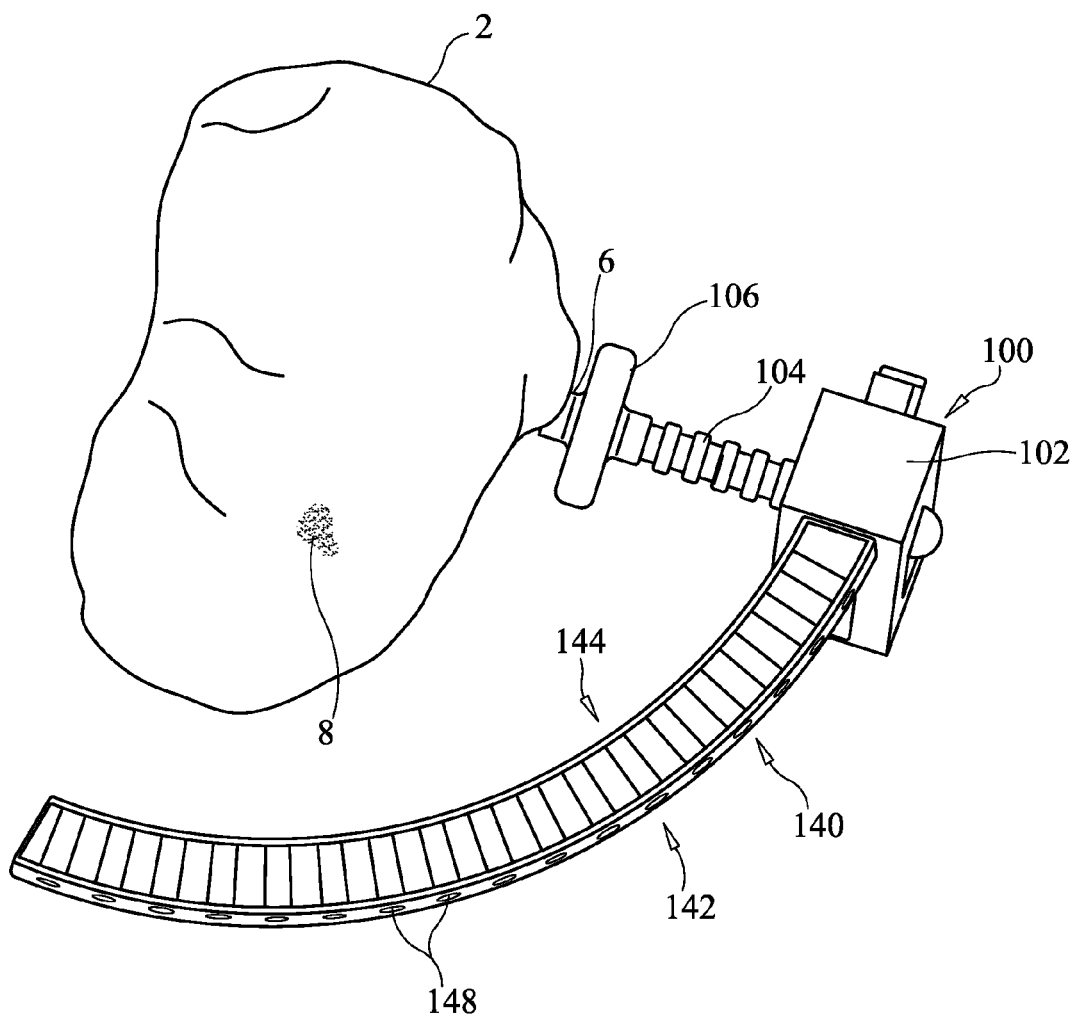
FIG. 5A shows a top-down view of yet another exemplary embodiment of an positioning instrument of the present disclosure.
Figure 5B:
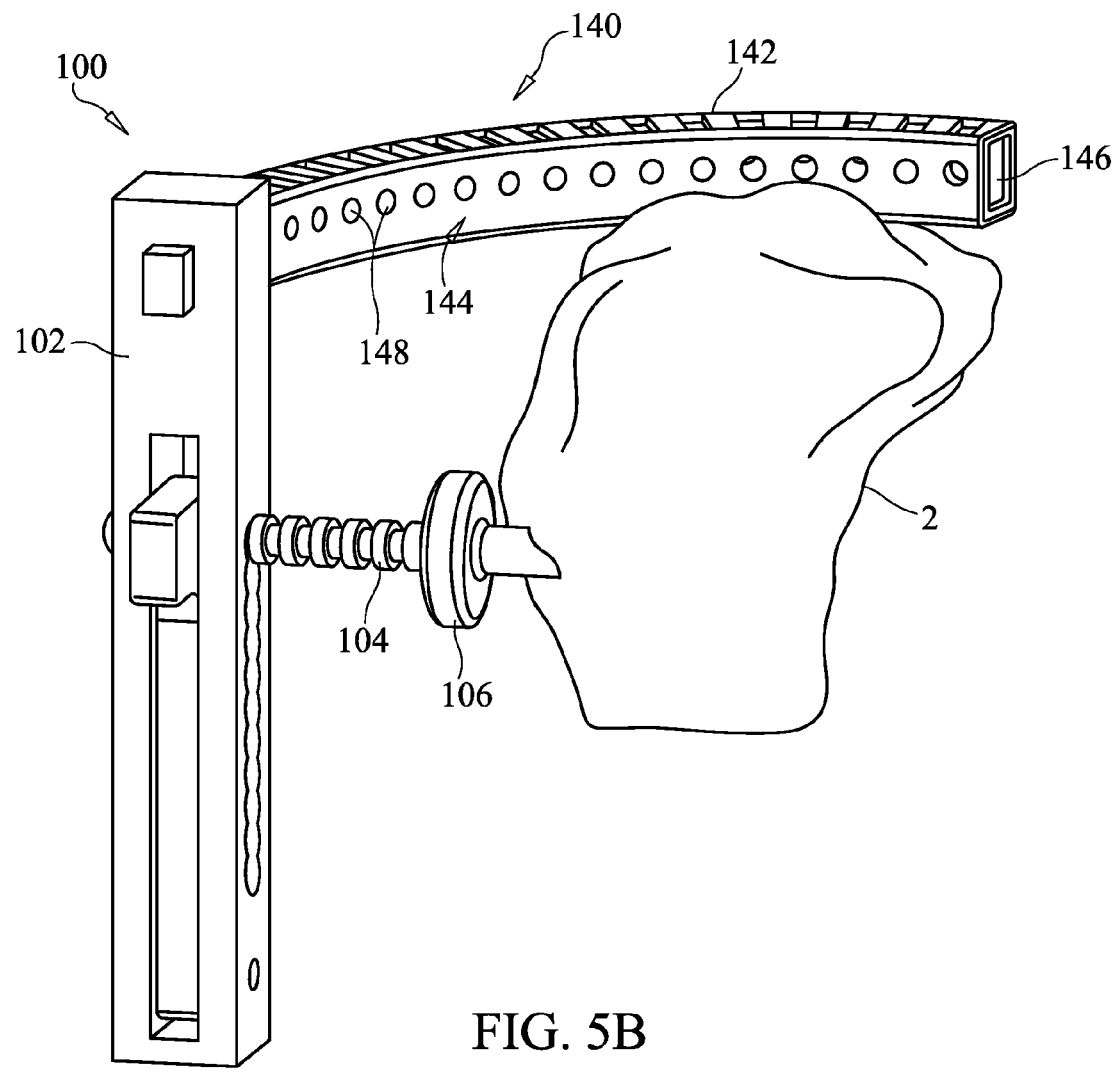
FIG. 5B shows a perspective side view of the positioning instrument of FIG. 5A.

FIG. 5A and FIG. 5B show another exemplary embodiment of a positioning instrument 100 in which the arm 104 is adjustable in height along the length of main body 102. An optional pointer or indicator (not shown) could be provided on the body 102 that points to the joint such that C-arm imaging can be used for vertical positioning of the instrument 100 during surgery. The pointer would be aligned with anatomy seen under C-arm such as the joint line, for example.

In this example, the rail 140 may be provided with a series of portals 148 that may be used as an alternative to the device portals 152 of alignment guide 150. Accordingly, in this embodiment no alignment guide 150 would be necessary and the surgeon could insert a device or tool directly through the rail 140 by way of these portals 148.

In one embodiment, the rail 140 could be configured to slidably adjust in the medial lateral direction with respect to the main body 102 to allow for fine tuning adjustment of the system 100. The adjustment would correspond to a medial or lateral shift of the template 20 from the G-A vertical line. In addition, the rail 140 could be straight instead of curved, and angled (i.e., angled linear rail), such that the portals 148 are parallel in arrangement. This would allow the use of a rotated X-Y coordinate grid on the template 20 rather than a radial grid. The linear rail 140 could be configured to angularly adjust relative to the main body 102. The main body 102 could be stabilized with a plurality of fixation pins to the bone, or additional arms 104 may be provided on the positioning instrument 100 for more stability as desired.

Figure 6:
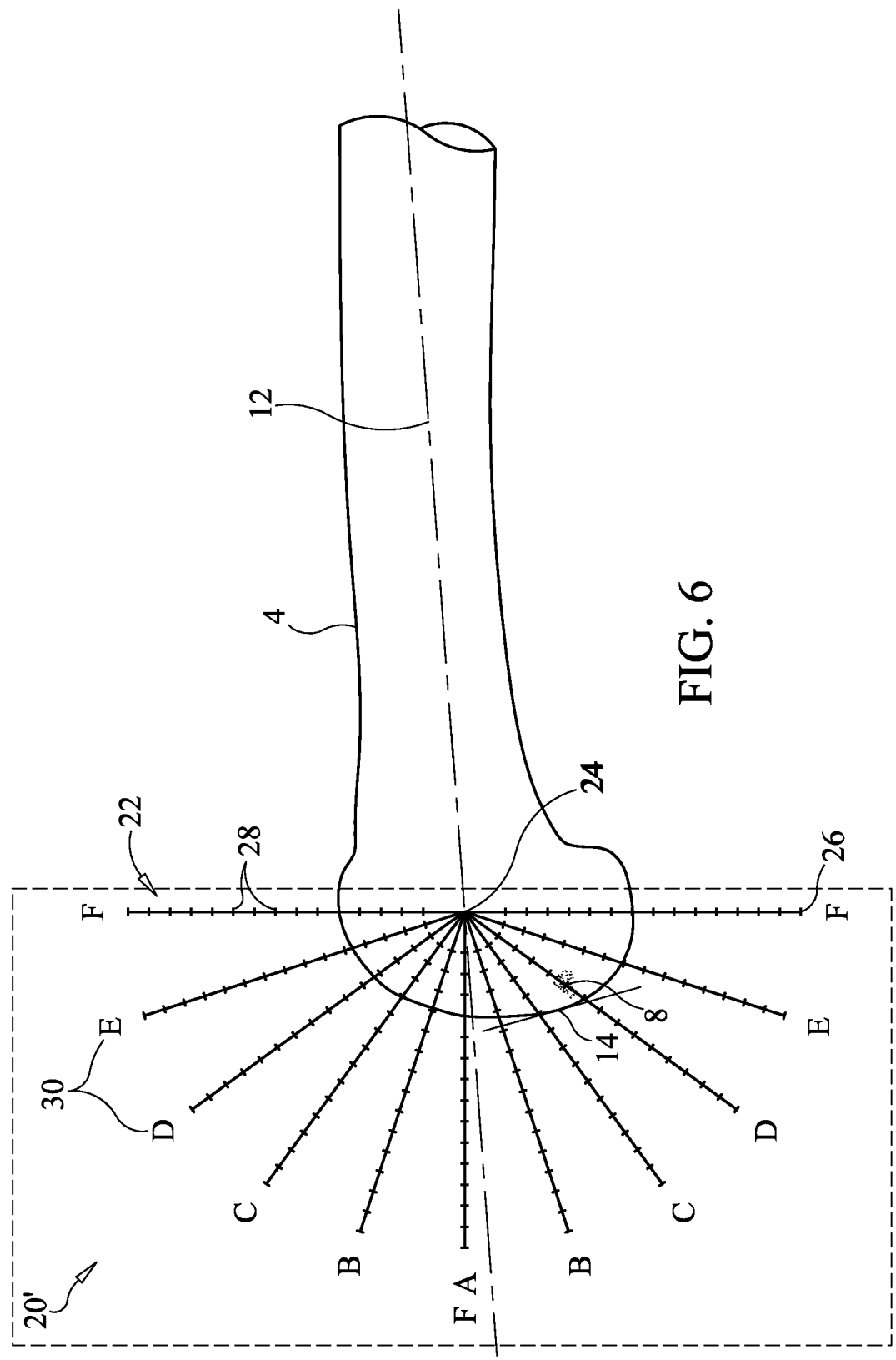
FIG. 6 shows an exemplary embodiment of a radial coordinate template superimposed over an image of a side view of a bone, such as the femur, having a defect.

FIG. 6 shows an exemplary embodiment of a template 20' configured for use with a femur 4. As shown, this template 20' is superimposed over an image of a side view of the femur 4 having a defect 8. Similar to template 20, the femoral template 20' comprises again a series of radial grid lines 22 spanning 180 degrees. Of course, it is understood that the template 20 may be configured with radial grid lines 22 that span any variety of degrees, such as for example 90, 270, 360, etc. as desired. The radial grid lines 22 extend from a common starting point at vertex 24, and terminate at an outer edge 26. In this embodiment, the radial grid lines 22 may be distributed in 18 degree intervals represented by indicia 30 labeled A to F.

In use, the axis F-A of the femoral template 20' is aligned with the axis 12 of the femur 4. The axis F-A is central to the distal portion of the shaft of the femur 4. Like template 20, the femoral template 20' provides for a set of three coordinates for locating the defect 8 in the femur 4 using the patient's own anatomical landmarks (i.e., axis of femoral shaft). For example, as shown in FIG. 6, the template 20' indicates a first coordinate, distance $d_3$, represented by the number of interval markings 28 between the vertex 24 to the joint line 14. The second coordinate may represent the angular component corresponding to radial grid line 22 as indicated by the indicia labeled "C" in this example. The third coordinate may represent the distance $d_4$ represented by the number of interval markings 28 between the vertex 24 to the location of the defect 8 along the "C" radial grid line 22. Accordingly, the example shown in FIG. 6 may have a coordinate set of 8-36-7.25, representing radial grid components and an angular component.

FIGS. 7A-7D show an exemplary use of another positioning instrument 200 of the present disclosure on a femur 4. As shown, the positioning instrument 200 may comprise an elongate body 202 terminating in a hub 208. The elongate body 202 may be attached along a portion of its length to braces 204, as illustrated in FIGS. 7A to 7D. Braces 204 are configured for use with a lower limb, such as a lower leg portion. It is understood, however, that other mechanisms may be employed instead of braces 204, such as for example, straps for securing the positioning instrument 200 to a lower leg portion.

Figure 7A:
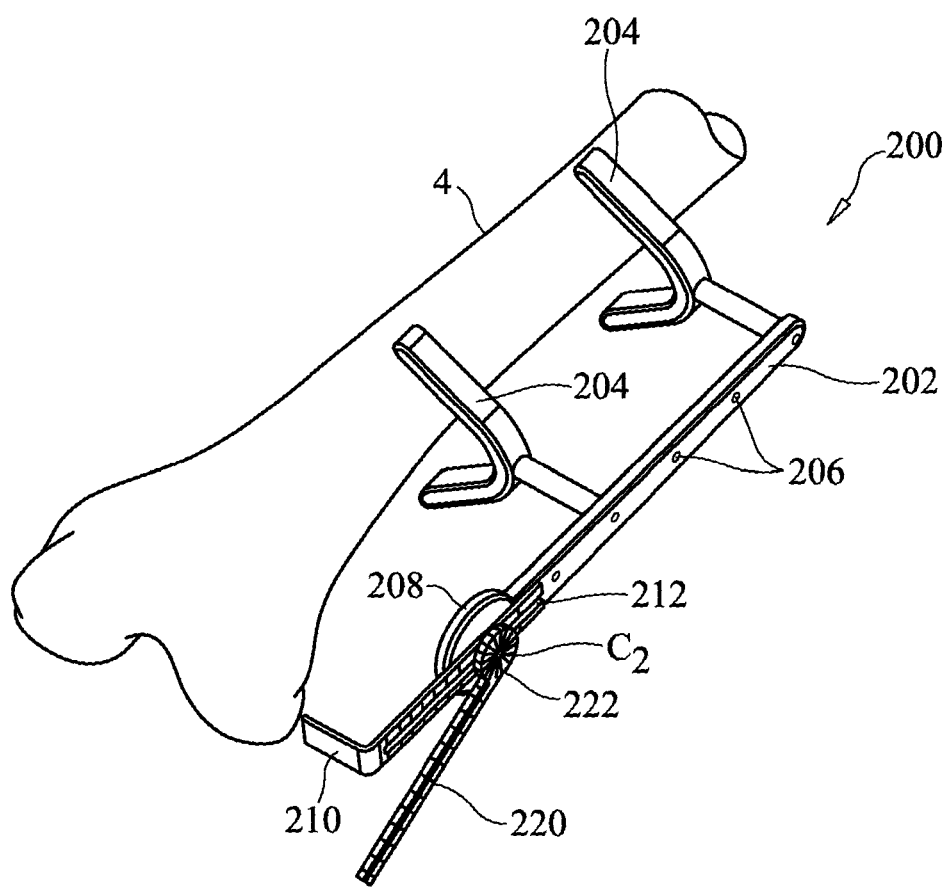
FIGS. 7A-7D show an exemplary use of another positioning instrument of the present disclosure on a femur.
Figure 7B:
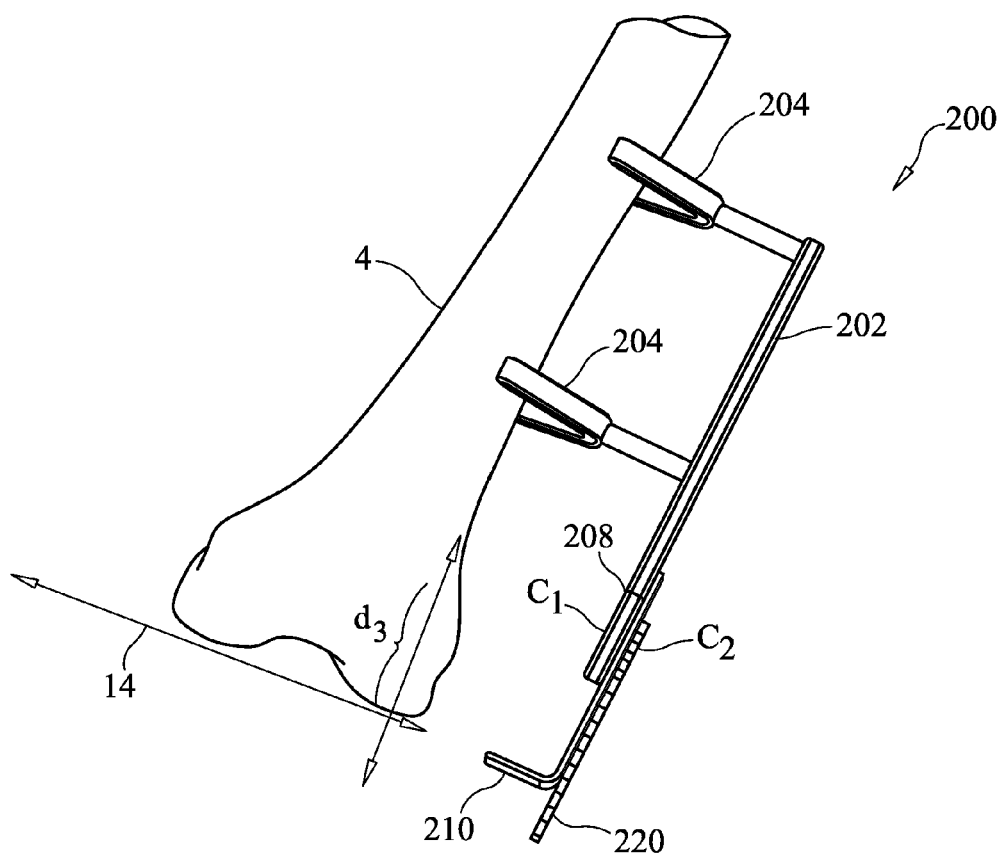
Figure 7C:
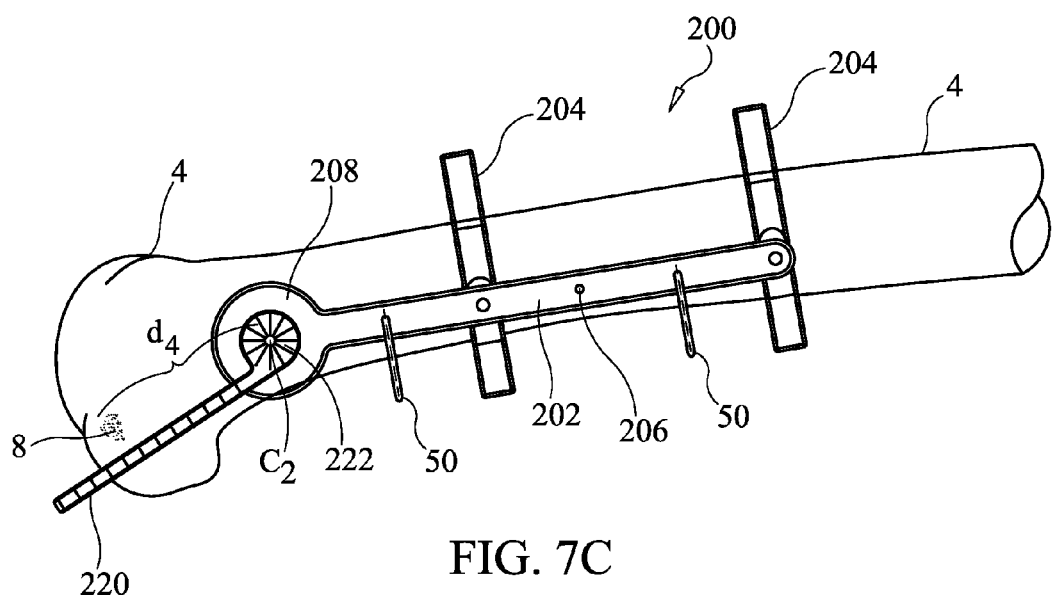
Figure 7D:
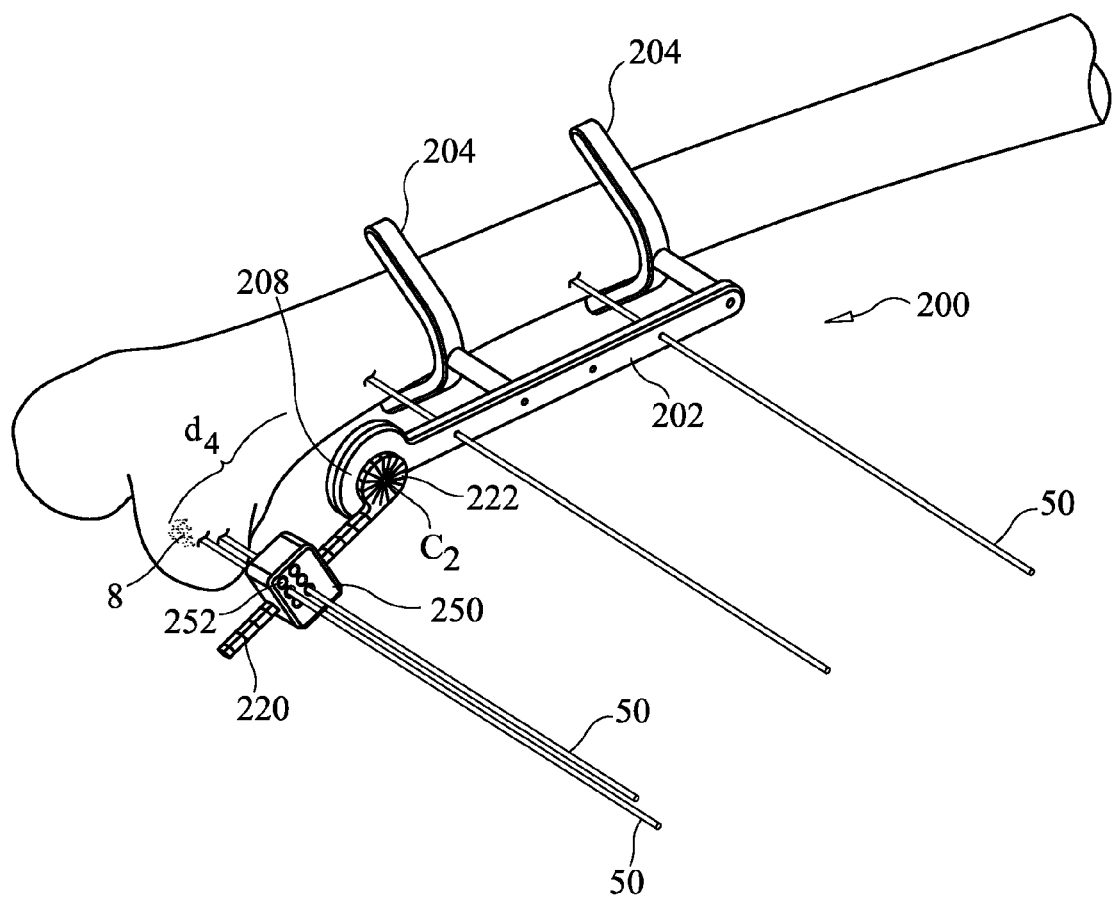

Tool-engaging holes 206 may also be provided on the elongate body 202 for receiving a tool such as a pin 50. In use, the center $C_1$ of hub 208 is placed at a distance $d_3$ from joint line 14 of the femur 4, as indicated by template 20' (see FIGS. 7A and 7B). In one example, a slidable arm 210 having an open-ended slot 212 for easy removal may be employed to position the elongate body 202 such that the center $C_1$ of hub 208 is a distance $d_3$ from the joint line 14, which can be determined from an anterior-posterior view of a C-arm image during the surgery. The elongate body 102 is aligned with the axis 12 of the femoral shaft. Pins 50 may be placed in order to secure the elongate body 102 to the femur 4 along its axis 12, as shown. After the elongate body 102 is secured, the slidable arm 210 may be removed, as shown in FIGS. 7C and 7D.

Extending from the hub 208 is a linear rail 220 at the angle specified by template 20'. The linear rail 220 comprises markings 224 along a circular portion 222 with a center $C_2$ that aligns with the center $C_1$ of hub 208. The linear rail 220 is configured to cooperate with an alignment guide 250. Alignment guide 250 may be configured with a slot to slidably receive linear rail 220, as shown. The alignment guide 250 may be positioned a distance $d_4$ from the center $C_1$ of hub 208. As shown, the alignment guide 250 may include device portals 252 that are arranged parallel to each other. It is understood that these portals 252 may be provided in other arrangements such as in an arc pattern.

The alignment guide 250 serves as a jig, or a box/frame for guiding a device to the defect. Each portal 252 has a predetermined distance and spatial relationship relative to the other portals 252. The portals 252 serve as spatial references or orientation or location markers for the clinician, and are configured to provide accurate and controlled delivery of a device to the defect. The portals 64 may be configured at any desired angle relative to the alignment guide 250. In one embodiment, the portals 252 may be angularly configured to guide, or direct, the device in a parallel direction relative to the top of the bone being treated, for example. In addition, the device portals 252 can include an anti-rotation feature (not shown). For example, the device portals 252 may be keyed, or shaped with a specific configuration that matches with a shape configuration of the device to be inserted. The keyed device portals 252 allow the device to enter and to move freely in a linear direction in and out of the portals 252, all the while preventing free rotation thereabout. Thus, the anti-rotation feature provides a further level of control for the clinician.

Figure 8A:
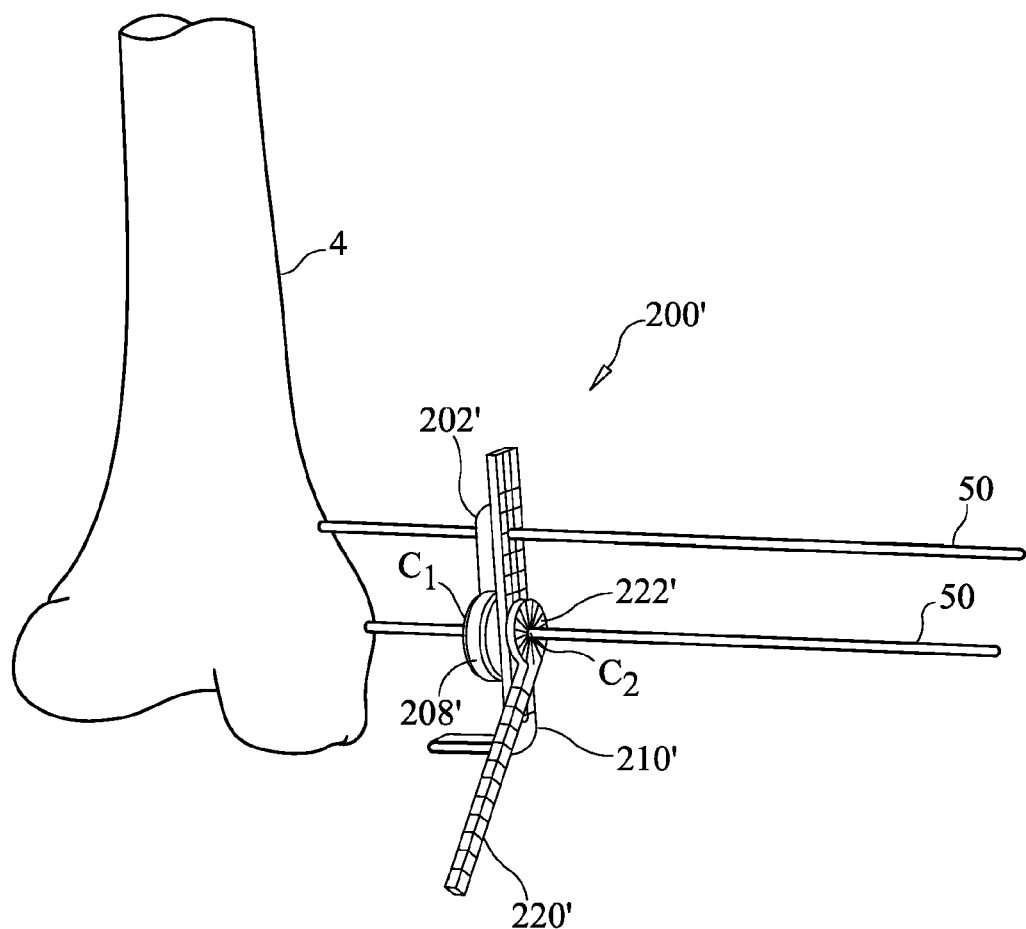
FIGS. 8A-8C show an exemplary use of yet another exemplary positioning instrument of the present disclosure on a femur.
Figure 8B:
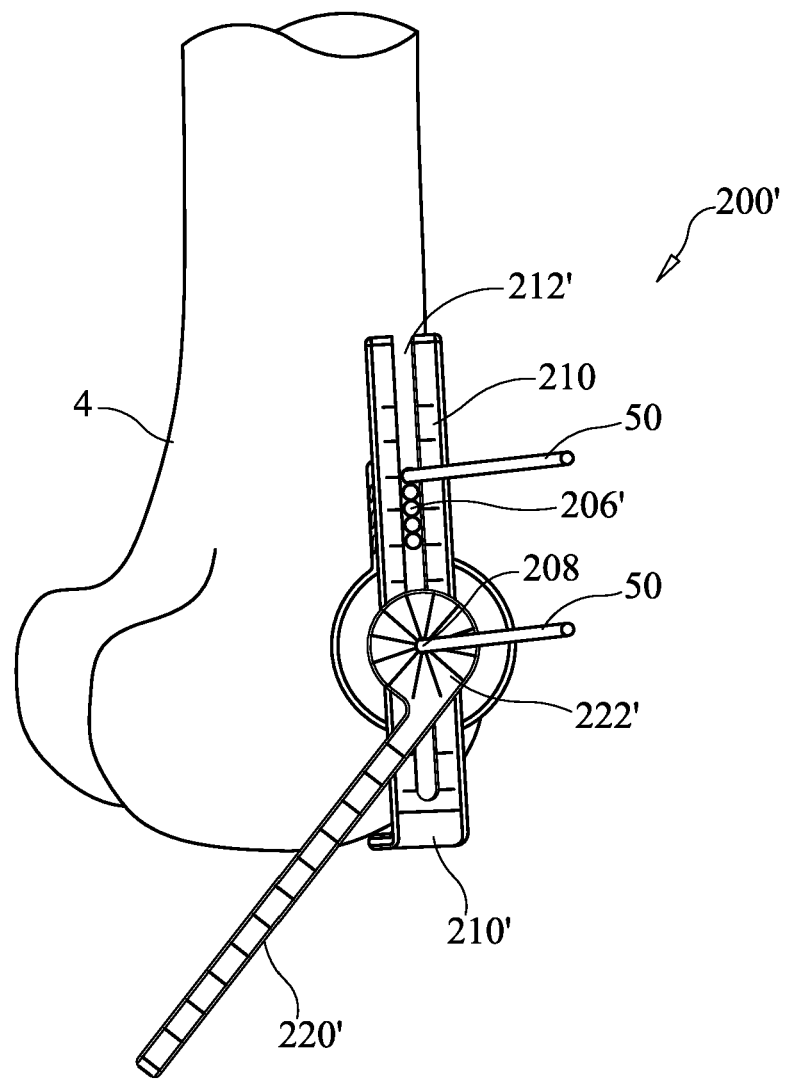
Figure 8C:
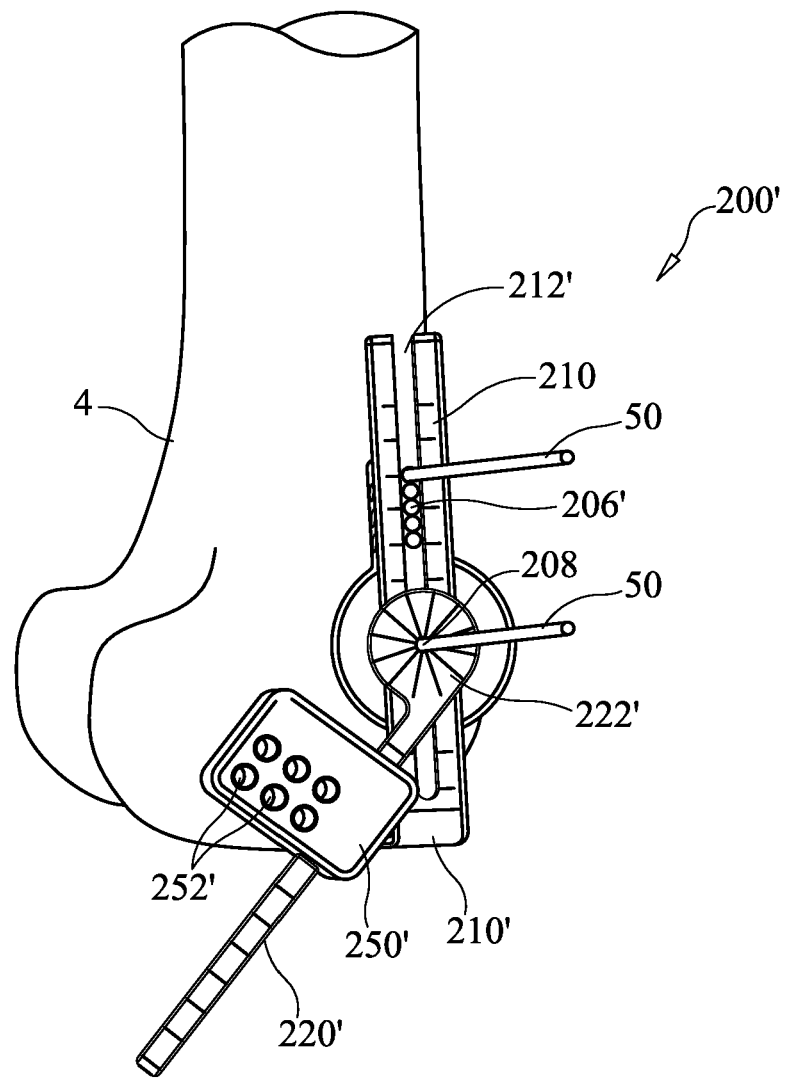

FIGS. 8A-8C show yet another positioning instrument 200' of the present disclosure on a femur 4. Positioning instrument 200' is similar in structure to positioning instrument 200' described above, with like elements having the same reference numerals followed by the mark "'". However, unlike positioning instrument 200, positioning instrument 200' may have a relatively short main body 202' for use without braces. Instead, main body 202' may include one or more tool-engaging holes 206' for receiving a tool such as pin 50. These pins 50 may extend through the tool-receiving holes 206' of the main body 202' and into the femur 4 to secure the instrumentation to the bone. In addition, the center $C_1$ of hub 208', along with the center $C_2$ of circular portion 222' of the linear rail 220' may include a tool-engaging hole 206 for also receiving a tool such as a pin 50, as shown in FIGS. 8A-8C.

In use, the positioning instrument 200' may be aligned to an anatomical landmark similar to positioning instrument 200.

In the case of this femur 4, the positioning instrument 200' may be aligned to the adductor tubercle on the distal femur, as shown. Pins 50 may be placed through the tool-engaging holes 206' of the centers $C_1$, $C_2$ of hub 208' and circular portion 222' of the main body 202' and linear rail 220', respectively. These pins 50 may extend through the open-ended slot 212' of the slidable arm 210' and into bone for securing the instrument 200' in place (see FIG. 8B). Similar to FIGS. 7A-7D, the slidable arm 210' of instrument 200' may be aligned to the joint line 14 of the femur 4 as identified through, for example, C-arm imaging during surgery. The positioning instrument 200' should be positioned so as to correspond to the template 20' for the femur 4, like in the previous example. Though not shown, the slidable arm 210' may be removed at this point if so desired.

After the positioning instrument 200' has been properly aligned and secured to the femur 4, the linear rail 220' can be positioned at an angle corresponding to the angular component of the three coordinate set determined by the femoral template 20' to map the location of the defect 8 on the femur 4. Next, alignment guide 250' may be slid onto the linear rail 220' as shown in FIG. 8C. The alignment guide 250' may be positioned such that the device portals 252' are aligned with the target site, or defect 8 according to a radial grid component of the three coordinate set. Then, one or more devices may then be inserted through the device portal 252' of the guide 250' and to the defect to effect the desired treatment. Positioning instrument 200' may be used percutaneously, and may serve as a fluoroscopic percutaneous device positioning instrument.

In the examples shown, the device may be a pin 50. However, the term "device" is used herein to refer generally to any number of implantable devices, materials and instruments suitable for bone treatment and/or repair. For example, the device may be an implantable device, an insertion tool, a drill bit, an injection needle, a catheter, or any other surgical instrument. The device may be marked with indicia or colored bands representing depth so that the clinician is better able to control the depth into the bone.

The coordinate mapping system 10 of the present disclosure provides the advantage of precise and repeated access to a target site from a variety of angles or trajectories. It is contemplated that the system 10 may be used to compact bone tissue at the target site from multiple approaches, or angles. For example, it is possible to use the system 10 to target the same area around the defect from different angles to clean up compressed bone tissue at the target site. By approaching the same defect using different trajectories, it is possible to create any number of geometric patterns of compacted bone tissue around or at the target site, such as for example, a starburst-like pattern.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A positioning instrument, comprising:
   a main body including a first hub portion and a first elongate portion extending from the first hub portion;
   a rail body including a second hub portion and a second elongate portion extending from the second hub portion, the rail body positioned along the main body such that a first hub portion center is aligned with a second hub portion center;
   an alignment guide being detachable and movable along a length of the rail body, the alignment guide including at least one device portal configured to guide a device into a bone; and
   a reference body including a third donate ion having a first end and a second end and a base portion, wherein the base portion extends from the first end and the second end includes an open-ended slot configured to receive a portion of the main body such that the main body is detachable and moveable with respect to the reference body.

2. The positioning instrument of claim 1, wherein the first elongate portion of the main body includes at least one tool engaging hole for receiving a tool.

3. The positioning instrument of claim 1, wherein the first hub portion center and the second hub portion center each include a tool engaging hole for receiving a tool.

4. The positioning instrument of claim 1, wherein the alignment guide includes a slot configured to receive the second elongate portion of the rail body.

5. The positioning instrument of claim 1, wherein the at least one device portal defines a trajectory for controlled delivery of a device to a target site of a bone.

6. The positioning instrument of claim 1, further including:
   at least one brace attachable to the first elongate portion of the main body, the at least one brace configured to secure the positioning instrument along a portion of a bone.

7. A positioning system for controlled delivery of a device to a target site of a bone, comprising:
   a positioning instrument, including:
      a main body including a first hub portion and a first elongate portion extending from the first hub portion;
      a rail body including a second hub portion and a second elongate portion extending from the second hub portion, the rail body positioned along the main body such that a first hub portion center is aligned with a second hub portion center; and
      an alignment guide being detachable and movable along a length of the rail body, the alignment guide including at least one device portal configured to guide a device into a bone; and
   a template configured to overlay an image of the bone having a defect at the target site, the template including a predefined grid for determining a set of coordinates to locate the target site using the positioning instrument.

8. The positioning instrument of claim 7, further including:
   a reference body including a third elongate portion and a base portion, wherein the base portion extends from a first end of the third elongate portion.

9. The positioning instrument of claim 8, wherein a second end of the third elongate portion includes an open-ended slot configured to receive a portion of the main body such that the main body is detachable and moveable with respect to the reference body.

10. The positioning system of claim 7, wherein the predefined grid includes a plurality of radial grid lines and a plurality of interval markings.

11. The positioning instrument of claim 10, wherein the second hub portion includes a first set of indicia configured to correspond to the plurality of radial grid lines and the second elongate portion includes a second set of indicia configured to correspond to the plurality of interval markings.

12. A method of accessing a target site near a defect in a bone, comprising:
   determining a set of coordinates of a location of the defect from a predefined grid;

providing a positioning instrument for controlled delivery of a device to the target site, the positioning instrument, including:

a main body including a first elongate portion and a first hub portion;

a rail body including a second elongate portion and a second hub portion, the rail body coupled to the main body such that a first hub portion center is aligned with a second hub portion center; and an alignment guide being detachable and movable along a length of the rail body, the alignment guide including at least one device portal configured to guide a device into a bone;

arranging the rail body at an angle corresponding to a first coordinate of the set of coordinates;

arranging the alignment guide at a position along the rail body corresponding to a second coordinate of the set of coordinates; and inserting a device through the at least one device portal to access the target site.

13. The method of claim 12 further including:

providing or obtaining a template having the predefined grid for determining the set of coordinates to locate the target site on the bone having the detect; and overlaying the template on an image of the bone, the template being aligned with an anatomical landmark on the bone.

14. The method of claim 12, wherein the positioning instrument further includes:

a reference body including a third elongate portion and a base portion extending from a first end of the third elongate portion, wherein a second end of the third elongate portion includes an open-ended slot configured to receive a portion of the main body such that the main body is detachable and moveable with respect to the reference body.

15. The method of claim 14, further including:

positioning the reference body along the bone such that the reference body is aligned with a joint line of the bone;

moving the main body within the open-ended slot until the first hub portion center is at a predetermined distance from the joint line; and securing the main body to the bone such that the first hub portion center is at the predetermined distance from the joint line.

16. The method of claim 12, wherein the predefined grid includes a plurality of radial grid lines and a plurality of interval markings, and wherein the first coordinate of the set of coordinates corresponds to a radial grid line and the second coordinate of the set of coordinates corresponds to an interval marking of the radial grid line.

17. The method of claim 16, wherein the second hub portion includes a first set of indicia corresponding to the plurality of radial grid lines and the second elongate portion includes a second set of indicia corresponding to the plurality of interval markings.

18. The method of claim 12, wherein the bone is at least one of a tibia and a femur, and wherein the anatomical landmark is at least one of a tubercle and a femoral shaft axis.

* * * * *